United States Patent
Ranawat et al.

(10) Patent No.: US 9,408,617 B2
(45) Date of Patent: Aug. 9, 2016

(54) METHOD FOR ORIENTING AN ACETABULAR CUP AND INSTRUMENTS FOR USE THEREWITH

(71) Applicant: NEW YORK SOCIETY FOR THE RUPTURED AND CRIPPLED MAINTAINING THE HOSPITAL FOR SPECIAL SURGERY, New York, NY (US)

(72) Inventors: Chitranjan S. Ranawat, Alpine, NJ (US); Joseph D. Lipman, New York, NY (US); Morteza Meftah, McLean, VA (US); David Mayman, New York, NY (US)

(73) Assignee: NEW YORK SOCIETY FOR THE RUPTURED AND CRIPPLED MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

(21) Appl. No.: 14/639,515

(22) Filed: Mar. 5, 2015

(65) Prior Publication Data

US 2015/0238272 A1 Aug. 27, 2015

Related U.S. Application Data

(62) Division of application No. 13/587,664, filed on Aug. 16, 2012, now Pat. No. 9,011,456.

(60) Provisional application No. 61/524,659, filed on Aug. 17, 2011.

(51) Int. Cl.
*A61B 17/17* (2006.01)
*A61F 2/46* (2006.01)
(Continued)

(52) U.S. Cl.
CPC ........... *A61B 17/1746* (2013.01); *A61F 2/4609* (2013.01); *G06F 19/3437* (2013.01);
(Continued)

(58) Field of Classification Search
CPC ..................... A61B 2017/568; A61B 2/30942; A61B 17/1746
See application file for complete search history.

(56) References Cited

U.S. PATENT DOCUMENTS

| 5,007,936 A | 4/1991 | Woolson |
| 5,880,976 A | 3/1999 | DiGioia III et al. |

(Continued)

FOREIGN PATENT DOCUMENTS

WO WO 2011/160008 12/2011

OTHER PUBLICATIONS

Hananouchi T, Saito M, Koyama T, Sugano N, Yoshikawa H. Tailor-made Surgical Guide Reduces Incidence of Outliers of Cup Placement. Clin Orthop Relat Res. Apr. 2010;468(4):1088-95, Epub Jul. 24, 2009. PubMed PMID: 19629605 Hananouchi T, Saito M, Koyama T, Sugano N, Yoshikawa H. Tailor-made Surgical Guide Reduces Incidence of Outliers of Cup Placement. Clin Orthop Relat Res. Apr. 2010;468(4):1088-95. Epub Jul. 24, 2009. PubMed PMID: 19629605.

*Primary Examiner* — Andrew Yang
(74) *Attorney, Agent, or Firm* — Leason Ellis LLP

(57) ABSTRACT

A patient-specific acetabular guide for use in orienting an acetabular component with respect to an acetabulum of a patient as part of a surgical procedure includes a body having a bottom contact surface that has a portion that is shaped and configured to initimately receive and interlockingly mate with an acetabular notch of the patient's acetabulum in accordance with a three-dimensional image of the acetabulum of the specific patient. The three-dimensional image can be in the form of a three-dimensional virtual model of the patient's acetabulum that is constructed at least in part on 3D image data of the pelvic region of the patient.

17 Claims, 21 Drawing Sheets

(51) Int. Cl.
*G06F 19/00* (2011.01)
*A61B 17/56* (2006.01)
*A61F 2/30* (2006.01)
*A61B 17/16* (2006.01)

(52) U.S. Cl.
CPC ....... *A61B17/1666* (2013.01); *A61B 2017/568* (2013.01); *A61B 2090/3983* (2016.02); *A61F 2/30942* (2013.01); *A61F 2002/30948* (2013.01); *A61F 2002/30952* (2013.01); *A61F 2002/4687* (2013.01)

(56) References Cited

U.S. PATENT DOCUMENTS

| | | |
|---|---|---|
| 7,572,295 B2 | 8/2009 | Steinberg |
| 7,660,623 B2 | 2/2010 | Hunter et al. |
| 2008/0255584 A1 | 10/2008 | Beverland et al. |
| 2008/0294265 A1 | 11/2008 | Warkentine et al. |
| 2008/0306558 A1 | 12/2008 | Hakki |
| 2009/0163922 A1 | 6/2009 | Meridew et al. |
| 2009/0254093 A1 | 10/2009 | White et al. |
| 2009/0316967 A1 | 12/2009 | Dardenne et al. |
| 2010/0016984 A1 | 1/2010 | Trabish |
| 2010/0185297 A1 | 7/2010 | Steinberg |
| 2010/0274253 A1 | 10/2010 | Ure |
| 2011/0093086 A1 | 4/2011 | Witt et al. |
| 2011/0184419 A1 | 7/2011 | Meridew et al. |
| 2011/0190775 A1* | 8/2011 | Ure ..................... A61F 2/4609 606/91 |
| 2012/0130279 A1 | 5/2012 | Stone |

* cited by examiner

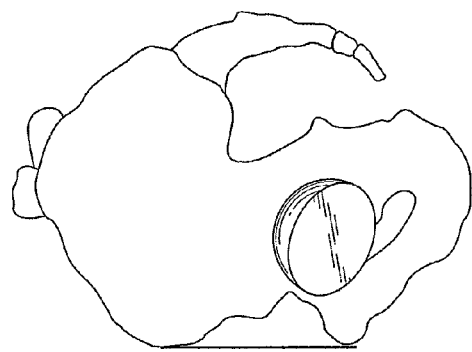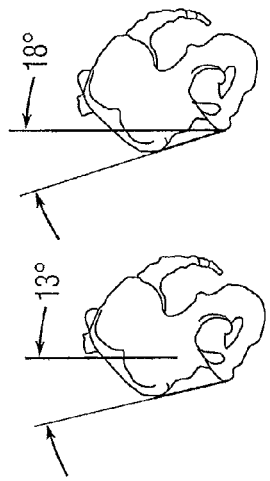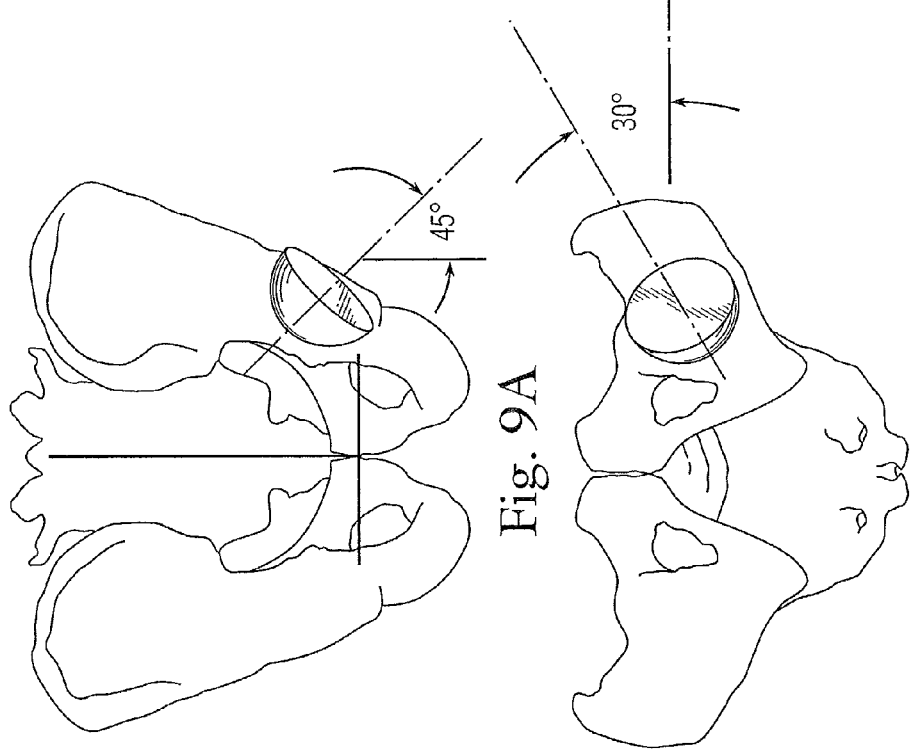
Fig. 9A Fig. 9B Fig. 9C Fig. 9D Fig. 9E

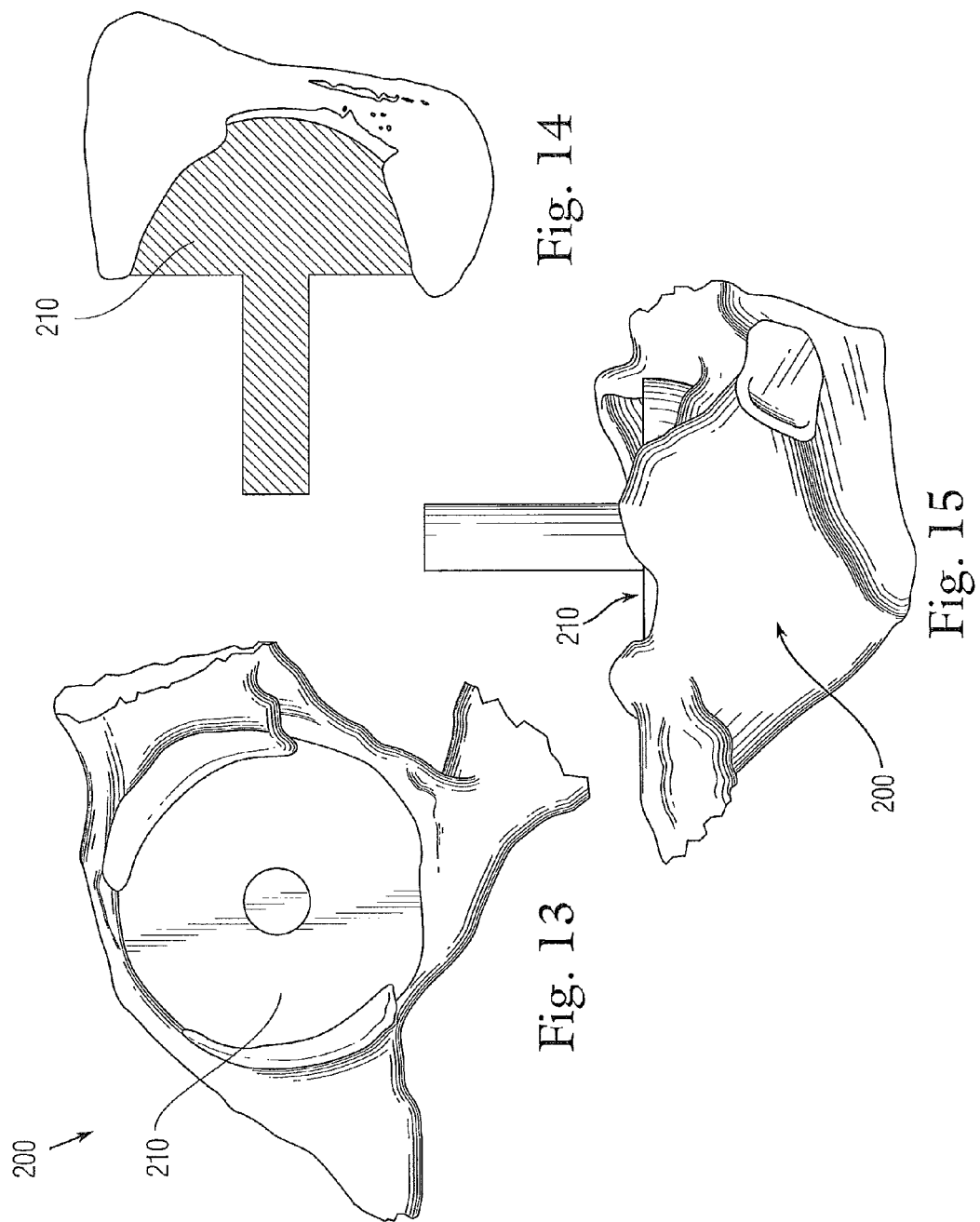

Sensor that
Can detect
Orientation of fiducial

Rigidly attach fiducial
With known coordinate system

METHOD FOR ORIENTING AN ACETABULAR CUP AND INSTRUMENTS FOR USE THEREWITH

CROSS-REFERENCE TO RELATED APPLICATION

The present application is a divisional of U.S. patent application Ser. No. 13/587,664, filed Aug. 16, 2012, which claims priority to U.S. patent application Ser. No. 61/524,659, filed Aug. 17, 2011, each of which is hereby incorporated by reference in its entirety.

TECHNICAL FIELD

The present invention relates generally to medical orientation and positioning devices and in particular to methods and tools for use in orientating surgical instruments, implements, implants, prosthetics and more specifically, to methods and instruments for orienting an acetabular component (cup) of a total hip replacement using a patient-specific guide that is formed in accordance with the present invention and is configured to guide the acetabular component into the acetabulum.

BACKGROUND

Correct positioning of surgical instruments and implants, used in a surgical procedure, with respect to the patient's anatomy is often a critical factor in achieving a successful outcome. In certain orthopaedic implant procedures, such as total hip replacement (THR), total knee arthroplasty (TKA) and total shoulder replacement (TSR), the optimal orientation of the surgical implant enhances the initial function and the long term operability of the implant.

With respect to THR, proper implantation of the acetabular component (cup) in total hip replacement (THR) is challenging. The hip is a ball and socket joint. In a normal hip, the femoral head is generally circular and rotates within the acetabulum which is also generally circular in shape. Ideally, the load transfer of body weight across the hip joint is distributed across the surface area of the femoral head and acetabulum. By distributing the loads across a maximum surface area of the femoral head and acetabulum, lower stresses result in the joint itself.

In a diseased hip, the ball and socket may be malformed and this can result in an uneven distribution of load. In the event of a deformed femoral head, load is transferred from the femoral head to the acetabulum along the periphery of the femoral head to the periphery of the acetabulum. As will be appreciated, this results in a transfer of load (imported by the body weight and muscle forces) to a surface area of much reduced size causing a high load per unit area value. This increased load per unit area causes damage to the joint by damaging the articular cartilage which over time can wear out.

From a biomechanical standpoint, successful hip function depends on a number of factors including the alignment of an acetabular cup. Accurate orienting of the cup is an important variable in reducing the risk of dislocation, bearing impingement, wear and edge loading, revisions, and long-term survivorship of the THR. Proper cup orientation can be determined by considering the appropriate abduction angle and anteversion of the component.

Various techniques involving bony landmarks or intra-operative jigs have been developed to allow the operating surgeon to produce accurate and reproducible cup placements. Alignment tools (guides) typically references the surgical table on which the patient rests. Conventionally, it is assumed that the patient's pelvis is parallel to the table, and the surgical table is parallel to the floor. Based on the proceeding assumptions, the ordinary orientation for most patients for the acetabular cup is between 40° and 45° of inclination and around 20° anteversion.

However, these techniques are subject to inaccuracies due to the variability of the patient's pelvic position on the operating table, degenerative lumbosacral disease, pelvic tilt, and the presence of osteophytes which makes bony landmarks harder to identify. For this reason, newer instruments utilizing computer assisted navigation or haptic robots have become more popular. However, these instruments are very expensive, require additional components (pins and rays) and have a long learning curve and thus are not entirely desirable for these reasons. In addition, as described below, a number of patient-specific guides have been developed by using the rim of the acetabulum to fit the patient-specific guide; however, the rim of the acetabulum is difficult to access as a result of it being covered in part by soft tissue and consequently, these guides suffer from this deficiency and others.

There is thus a need to overcome these deficiencies and provide an improved method(s) and instrument(s) for orienting the acetabular component (cup) during and as part of a total hip replacement procedure.

SUMMARY

In one embodiment of the present invention, a patient-specific acetabular guide for use in orienting an acetabular component with respect to an acetabulum of a patient as part of a surgical procedure is provided. The patient-specific guide includes a body having a bottom contact surface that has a portion that is shaped and configured to initimately receive and interlockingly mate with an acetabular notch of the patient's acetabulum in accordance with a three-dimensional image of the acetabulum of the specific patient. The three-dimensional image can be in the form of a three-dimensional virtual model of the patient's acetabulum that is constructed at least in part on 3D image data of the pelvic region of the patient.

In accordance with one embodiment, a method of pre-operatively planning the implantation of a patient-specific acetabular component comprising the steps of: (1) obtaining three-dimensional image data of a pelvic region of the patient; (2) using the obtained image data to determine a selected orientation of the acetabular component with respect to an acetabulum of the patient, the selected orientation being defined by a center longitudinal axis; and (3) constructing a three-dimensional model of an acetabular guide from the obtained image data, wherein the three-dimensional model of the acetabular guide includes a contact surface that is shaped to substantially match an acetabular notch of the patient's acetabulum, wherein a center longitudinal axis of the acetabular guide is co-linear or parallel to the center axis of the acetabular component.

In accordance with one embodiment, a method for implanting an acetabular component in an acetabulum of a patient comprising the steps of: (1) inspecting a pre-operative plan including a three-dimensional image of the specific patient; (2) selecting a patient-specific anteversion angle and an inclination angle for the acetabular component so as to define a prescribed orientation for the acetabular component; (3) constructing a patient-specific acetabular guide having a contact surface that is made to conform to an acetabular notch of the acetabular of the patient in accordance with the three-dimensional image of the specific patient and be oriented in the prescribed orientation; (4) orienting the patient-specific acetabular guide in the acetabulum of the specific patient such that the contact surface interlocks with the acetabular notch of the patient's acetabulum; (5) using the patient-specific guide to orient an axis pin that is parallel to a center axis of the acetabular guide; and (6) implanting the acetabular component using the axis pin as a reference for the component orientation.

The method also includes the steps of a inserting a pin guide into an opening formed in a surface of the patient-specific acetabular guide that is opposite the contact surface. The pin guide has a pin receiving section that has a bore defined by a first axis that is parallel to an axis of the handle of the patient-specific acetabular guide. An axis pin is inserted through the bore and the axis pin is fixedly attached to the bone. The pin guide is removed from the patient-specific acetabular guide and the patient-specific acetabular guide is removed from the acetabulum, whereby the axis pin defines a reference axis for orienting the acetabulum component within the acetabulum.

In an alternative embodiment, a pin is attached to a superior portion of the acetabulum and a pin reference device is assembled to the pin by coupling a first section of the device to the fixed pin. The first section of the pin reference device has two degrees of freedom relative to the pin and the pin reference device further includes a rod that is pivotally attached to the first section and has one degree of freedom relative thereto. The rod comprises the first reference member and defines the reference axis for orienting the acetabulum component within the acetabulum. As described herein, the pin reference device includes locking means to allow it to be locked in place once it is properly oriented.

BRIEF DESCRIPTION OF DRAWING FIGURES

FIG. 9A-9E show an acetabular component oriented relative to the acetabulum according to a second method once the pelvis has been properly oriented;

FIG. 13 is a top plan view of the acetabulum showing the result of a first Boolean operation between the acetabular guide of FIG. 10 and the offset acetabulum showing modification to the guide to remove material interfering with bone (the original articular surface of the acetabulum is not shown in this figure);

FIG. 14 is a cross-sectional view of FIG. 13;

FIG. 15 is a side elevation view of FIG. 13;

DETAILED DESCRIPTION OF CERTAIN EMBODIMENTS

In accordance with the present invention and as discussed below, a method and associated instrument(s) are provided to simply, yet accurately, orient the acetabular component of a total hip replacement (THR) using both pre-operative imaging, and a patient-specific instrument that is used at the time of the surgical procedure. As described herein, the orientation of the acetabular component is determined using any one of a number of techniques that are described in detail herein.

There are three bones of the os coxae (hip bone) that come together to form the acetabulum. Contributing a little more than two-fifths of the structure is the ischium, which provides lower and side boundaries to the acetabulum. The ilium forms the upper boundary, providing a little less than two-fifths of the structure of the acetabulum. The rest is formed by the pubis, near the midline. It is bounded by a prominent uneven rim, which is thick and strong above, and serves for the attachment of the acetabular labrum, which reduces its opening, and deepens the surface for formation of the hip joint. At the lower part of the acetabulum is the acetabular notch, which is continuous with a circular depression, the acetabular fossa, at the bottom of the cavity of the acetabulum. The rest of the acetabulum is formed by a curved, crescent-moon shaped surface (the lunate surface) where the joint is made with the head of the femur. Its counterpart in the pectoral girdle is the glenoid fossa.

Figure 4:
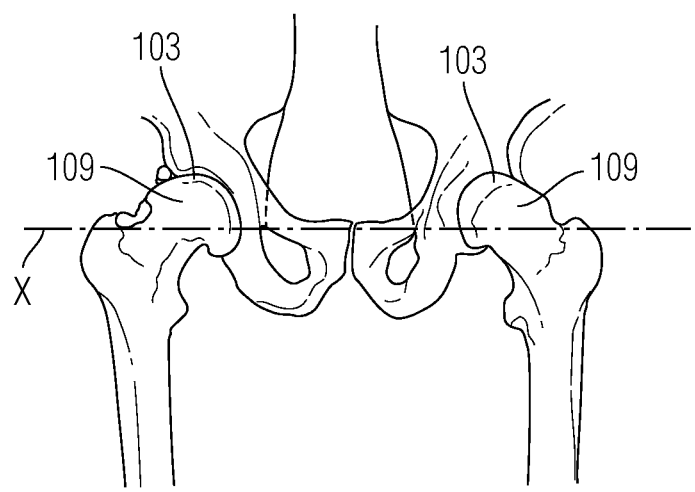
FIG. 4 is an image of a pelvic region of a patient.

FIG. 4 generally shows the acetabulum as 103 and the femur head as 109.

In one aspect, the present invention is directed to a patient-specific acetabular guide for use in orthopedic surgery, such as, for example, in joint replacement (THR), etc. As discussed below, the patient-specific acetabular guide can be used either with conventional implant components (e.g., an acetabular shell (cup)) or patient-specific implant components prepared with computer-assisted image methods.

As mentioned above, the method of the present invention is based at least in part on pre-operating (pre-operative) imaging. As is understood in the art, pre-operative imaging has a number of different purposes and generally is performed in order to subsequently guide the surgeon during the surgical procedure, allow for patient-specific tools and/or implants to be formed, etc.

More particularly, the present invention is part of a computer system 10 for designing and constructing a patient-specific acetabular guide and its use in an orthopedic surgical procedure in which an acetabular component is prepared, orientated and implanted. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather are to provide an understandable description of the systems and methods.

Figure 1:
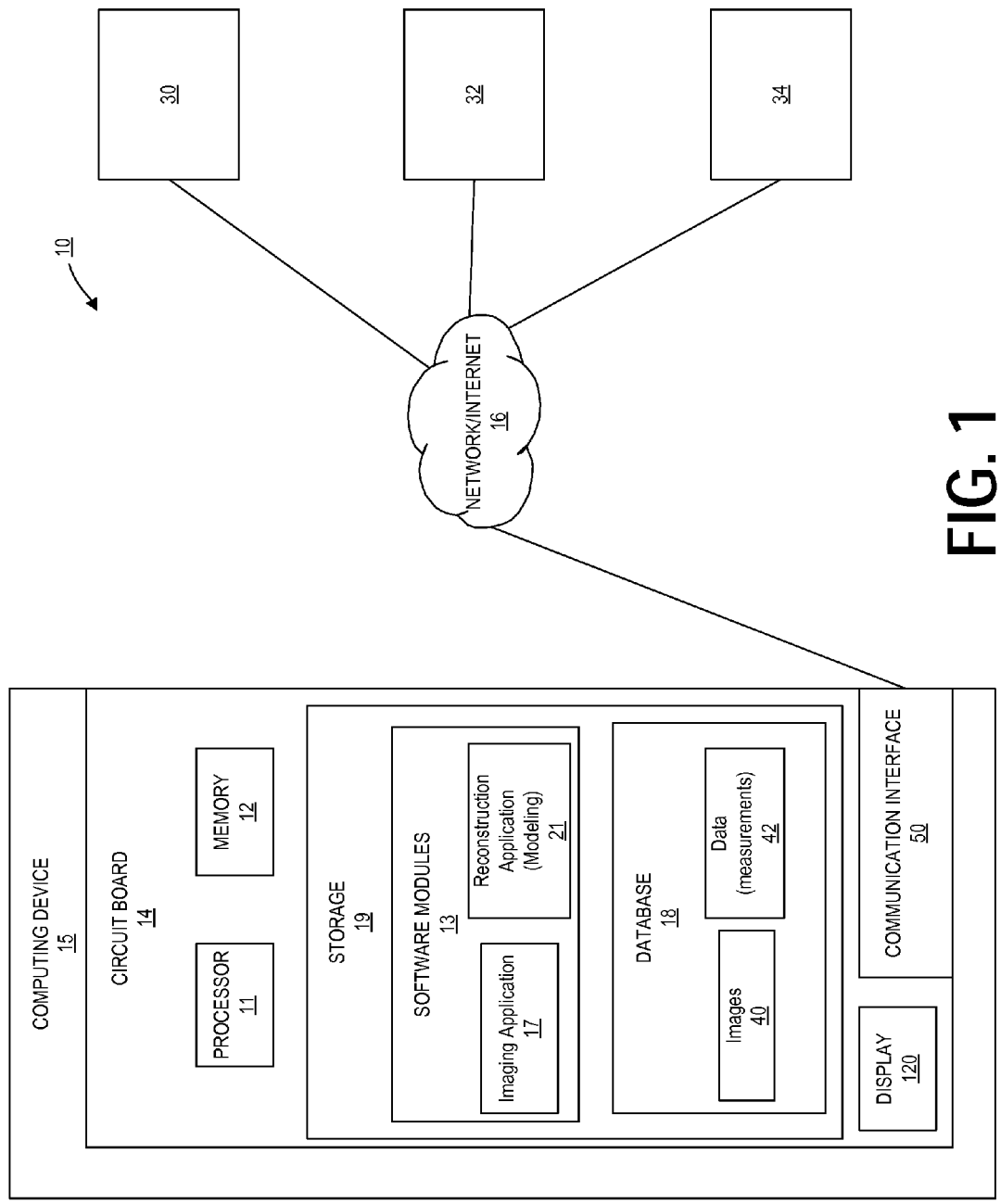
FIG. 1 is a schematic view of a computer system in accordance with the present invention.

An exemplary computer system is shown as a block diagram in FIG. 1 which is a high-level diagram illustrating an exemplary configuration of a system 10 for performing pre-operative imaging and computer modeling operations and for designing and constructing a patient-specific acetabular guide for use in orienting the acetabular component. In one implementation, computing device 15 can be a personal computer or server. In other implementations, computing device 15 can be a tablet computer, a laptop computer, or a mobile device/smartphone, though it should be understood that computing device 15 of the present system 10 can be practically any computing device and/or data processing apparatus capable of embodying the systems and/or methods described herein.

Computing device 15 of the system 10 includes a circuit board 14, such as a motherboard, which is operatively connected to various hardware and software components that serve to enable operation of the system 10 as described herein and in particular, are configured to provide the imaging and computer graphic modeling operations described herein. The circuit board 14 is operatively connected to a processor 11 and a memory 12. Processor 11 serves to execute instructions for software that can be loaded into memory 12. Processor 11 can be a number of processors, a multi-processor core, or some other type of processor, depending on the particular implementation. Further, processor 11 can be implemented using a number of heterogeneous processor systems in which a main processor is present with secondary processors on a single chip. As another illustrative example, processor 11 can be a symmetric multi-processor system containing multiple processors of the same type.

Preferably, memory 12 and/or storage 19 are accessible by processor 11, thereby enabling processor 11 to receive and execute instructions stored on memory 12 and/or on storage 19. Memory 12 can be, for example, a random access memory (RAM) or any other suitable volatile or non-volatile computer readable storage medium. In addition, memory 12 can be fixed or removable. Storage 19 can take various forms, depending on the particular implementation. For example, storage 19 can contain one or more components or devices such as a hard drive, a flash memory, a rewritable optical disk, a rewritable magnetic tape, or some combination of the above. Storage 19 also can be fixed or removable.

One or more software modules 13 are encoded in storage 19 and/or in memory 12. The software modules 13 can comprise one or more software programs or applications having computer program code or a set of instructions executed in processor 11. Such computer program code or instructions for carrying out operations for aspects of the systems and methods disclosed herein can be written in any combination of one or more programming languages, including an object oriented programming language such as Java, Smalltalk, C++, Python, and JavaScript or the like and conventional procedural programming languages, such as the "C" programming language or similar programming languages. The program code can execute entirely on computing device 15, partly on computing device 15, as a stand-alone software package, partly on computing device 15 and partly on a remote computer/device, or entirely on the remote computer/device or server. In the latter scenario, the remote computer can be connected to computing device 15 through any type of network, including a local area network (LAN) or a wide area network (WAN), or the connection can be made to an external computer (for example, through the Internet 16 using an Internet Service Provider).

One or more software modules 13, including program code/instructions, are located in a functional form on one or more computer readable storage devices (such as memory 12 and/or storage 19) that can be selectively removable. The software modules 13 can be loaded onto or transferred to computing device 15 for execution by processor 11. It can also be said that the program code of software modules 13 and one or more computer readable storage devices (such as memory 12 and/or storage 19) form a computer program product that can be manufactured and/or distributed in accordance with the present invention, as is known to those of ordinary skill in the art.

It should be understood that in some illustrative embodiments, one or more of software modules 13 can be downloaded over a network to storage 19 from another device or system via communication interface 15 for use within system 10. For instance, program code stored in a computer readable storage device in a server can be downloaded over a network from the server to system 10.

Preferably, included among the software modules 13 is an imaging application 17 and a reconstruction (modeling) application 21, each of which is executed by processor 11. It will be appreciated that other applications can be present. During execution of the software modules 13, and specifically the applications 17, 21, the processor 11 configures the circuit board 14 to perform various operations relating to product arrangement determination with computing device 15, as will be described in greater detail below. It should be understood that while software modules 13 and/or applications 17, 21 can be embodied in any number of computer executable formats, in certain implementations software modules 13 and/or applications 17, 21 comprise one or more applications that are configured to be executed at computing device 15 in conjunction with one or more applications or 'apps' executing at remote devices, such as computing device(s) 30, 32, and/or 34 and/or one or more viewers such as internet browsers and/or proprietary applications. Furthermore, in certain implementations, software modules 13 and/or applications 17, 21 can be configured to execute at the request or selection of a user of one of computing devices 30, 32, and/or 34 (or any other such user having the ability to execute a program in relation to computing device 15, such as a network administrator), while in other implementations computing device 15 can be configured to automatically execute software modules 13 and/or applications 17, 21 without requiring an affirmative request to execute. It should also be noted that while FIG. 1 depicts memory 12 oriented on circuit board 14, in an alternate arrangement, memory 12 can be operatively connected to the circuit board 14. In addition, it should be noted that other information and/or data relevant to the operation of the present systems and methods (such as database 18) can also be stored on storage 19, as will be discussed in greater detail below.

Also preferably stored on storage 19 is database 18. As will be described in greater detail below, database 18 contains and/or maintains various data items and elements that are utilized throughout the various operations the system 10, including but not limited to image files 40, data/measurements 42, etc., as will be described in greater detail herein. It should be noted that although database 18 is depicted as being configured locally to computing device 15, in certain implementations database 18 and/or various of the data elements stored therein can be located remotely (such as on a remote device or server—not shown) and connected to computing device 15 through network 16, in a manner known to those of ordinary skill in the art.

Communication interface 50 is also operatively connected to circuit board 14. Communication interface 50 can be any interface that enables communication between the computing device 15 and external devices, machines and/or elements. Preferably, communication interface 50 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting computing device 15 to other computing devices and/or communication networks such as private networks and the Internet. Such connections can include a wired connection or a wireless connection (e.g. using the 802.11 standard) though it should be understood that communication interface 50 can be practically any interface that enables communication to/from the circuit board 14.

In the description that follows, certain embodiments and/or arrangements are described with reference to acts and symbolic representations of operations that are performed by one or more devices, such as the system 10 of FIG. 1. As such, it will be understood that such acts and operations, which are at times referred to as being computer-executed or computer-implemented, include the manipulation by processor 11 of electrical signals representing data in a structured form. This manipulation transforms the data and/or maintains them at locations in the memory system of the computer (such as memory 12 and/or storage 19), which reconfigures and/or otherwise alters the operation of the system in a manner understood by those skilled in the art. The data structures in which data are maintained are physical locations of the memory that have particular properties defined by the format of the data. However, while an embodiment is being described in the foregoing context, it is not meant to provide architectural limitations to the manner in which different embodiments can be implemented. The different illustrative embodiments can be implemented in a system including components in addition to or in place of those illustrated for the system 10. Other components shown in FIG. 1 can be varied from the illustrative examples shown. The different embodiments can be implemented using any hardware device or system capable of running program code. In another illustrative example, the system 10 can take the form of a hardware unit that has circuits that are manufactured or configured for a particular use. This type of hardware can perform operations without needing program code to be loaded into a memory from a computer readable storage device to be configured to perform the operations.

For example, computing device 15 can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules 13 can be omitted because the processes for the different embodiments are implemented in a hardware unit.

In still another illustrative example, computing device 15 can be implemented using a combination of processors found in computers and hardware units. Processor 11 can have a number of hardware units and a number of processors that are configured to execute software modules 13. In this example, some of the processors can be implemented in the number of hardware units, while other processors can be implemented in the number of processors.

In another example, a bus system can be implemented and can be comprised of one or more buses, such as a system bus or an input/output bus. Of course, the bus system can be implemented using any suitable type of architecture that provides for a transfer of data between different components or devices attached to the bus system. Additionally, communications interface 50 can include one or more devices used to transmit and receive data, such as a modem or a network adapter.

Embodiments and/or arrangements can be described in a general context of computer-executable instructions, such as program modules, being executed by a computer. Generally, program modules include routines, programs, objects, components, data structures, etc., that perform particular tasks or implement particular abstract data types.

It should be further understood that while the various computing devices and machines referenced herein, including but not limited to computing device 15, computing devices 30, 32, and 34 are referred to herein as individual/single devices and/or machines, in certain implementations the referenced devices and machines, and their associated and/or accompanying operations, features, and/or functionalities can be arranged or otherwise employed across any number of devices and/or machines, such as over a network connection, as is known to those of skill in the art.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and arrangements of the present systems and methods provide a computer implemented method, computer system, and computer program product for determining product arrangements. The block diagram in the figures illustrates the architecture, functionality, and operation of possible implementations of systems, methods and computer program products according to various embodiments and arrangements. In this regard, each block in the block diagram can represent a module, segment, or portion of code, which comprises one or more executable instructions for implementing the specified logical function(s). It should also be noted that, in some alternative implementations, the functions noted in the block may occur out of the order noted in the figure. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 2:
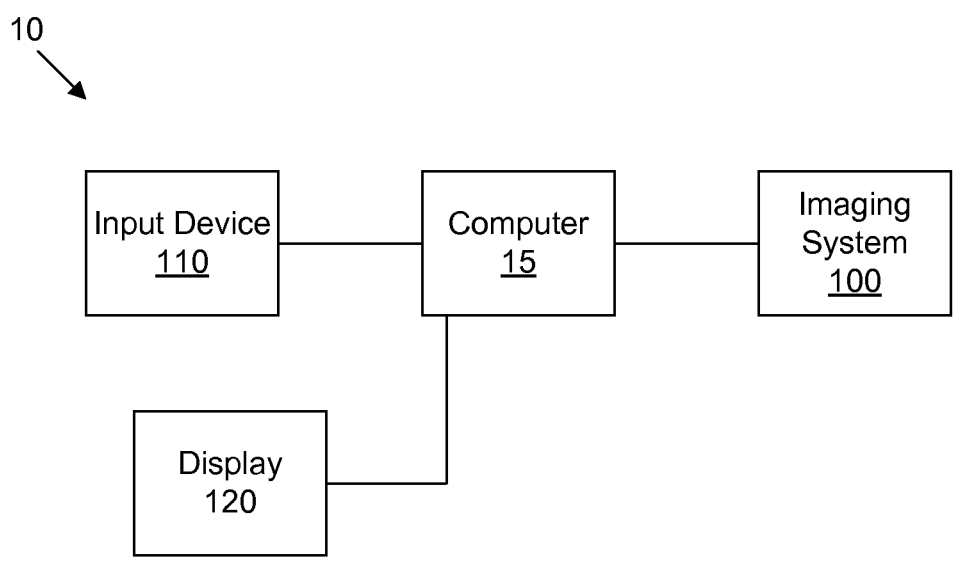
FIG. 2 is a schematic of various components of the present system.

FIG. 2 is a block diagram of certain select components of the system 10 in accordance with the present invention. More specifically, the computer 15 of the system 10 is coupled to an imaging system 100 and further includes an input device 110 and one or more displays 120.

As described herein, the imaging system 100 can be a conventional imaging device for providing medical images, such as X-rays, fluoroscopic, CT, MRI, etc., of a patient's anatomical regions. The display 120 can be in the form of a conventional device for displaying images obtained by the imaging system 100 and for displaying virtual representations of at least one of a portion of the patient and an instrument (tool) in 3D space on an image of the patient, where the virtual representations are based on data obtained from the imaging system 100 and optionally based on other measurement or data collected during the procedure. The display 120 can thus be in the form of a monitor, etc. The input device 110 can be in the form of a conventional device for inputting data, instruction, commands, etc. For example, the input device 110 can be in the form of a keyboard, mouse, touch screen, voice recognition system, etc.

As discussed above, the present system 10 can be thought of as including a number of distinct phases in both a pre-operative setting and surgical setting. These phases are discussed below; however, the breakdown and labeling of the different phases is merely for instructive and illustrative purposes only and is not limiting of the scope of the present invention.

Pre-Operative Phase

In one aspect, pre-operative, imaging can include any one of a number of different types of imaging procedures performed by the imaging system 100. As discussed herein, the pre-operative imaging can involve both two-dimensional (2D) images, such as a radiograph, of an area of interest, such as the pelvic region; and includes three-dimensional (3D) imaging data of the pelvic region, and the affected proximal femur and ipsilateral knee.

It will be understood that the imaging application 17 of the computer device 15 is designed to process the information and images obtained from the imaging system 100. A 3D scan can be performed and in combination with computer software (such as applications 17, 21 or the like) allows one to obtain three dimensional images of the patient's anatomy using scans (e.g., MRI or CT scans) of the patient's anatomy. As discussed in detail below, the patient-specific tools or guides (e.g., the patient-specific acetabular guide) and templates can be provided and designed by various CAD programs and/or software programs that allow the images and models to be manipulated.

Patient-specific guides and implants are generally configured to match the anatomy of a specific patient. As described herein, the patient-specific acetabular guide is generally formed using computer imaging and software based on the patient's 3-D anatomic image and have an engagement surface that is made to conformingly contact and match a three-dimensional image of the patient's bone surface (with or without cartilage or other soft tissue), by the computer methods discussed above and herein.

In the preoperative planning stage for a joint replacement procedure (such as THR), an MRI scan or a series of CT scans of the relevant anatomy of the patient, such as, for example, the pelvis and the leg, etc., can be performed at a medical facility or doctor's office. The scan data obtained as DICOM data an can be used to construct a three-dimensional image of the joint and provide an initial implant fitting and alignment in a computer file form or other computer representation as discussed below with respect to a different subsequent phase of the present method in which the instrument (tool or guide) is designed.

Initial Imaging Phase

Figure 3:
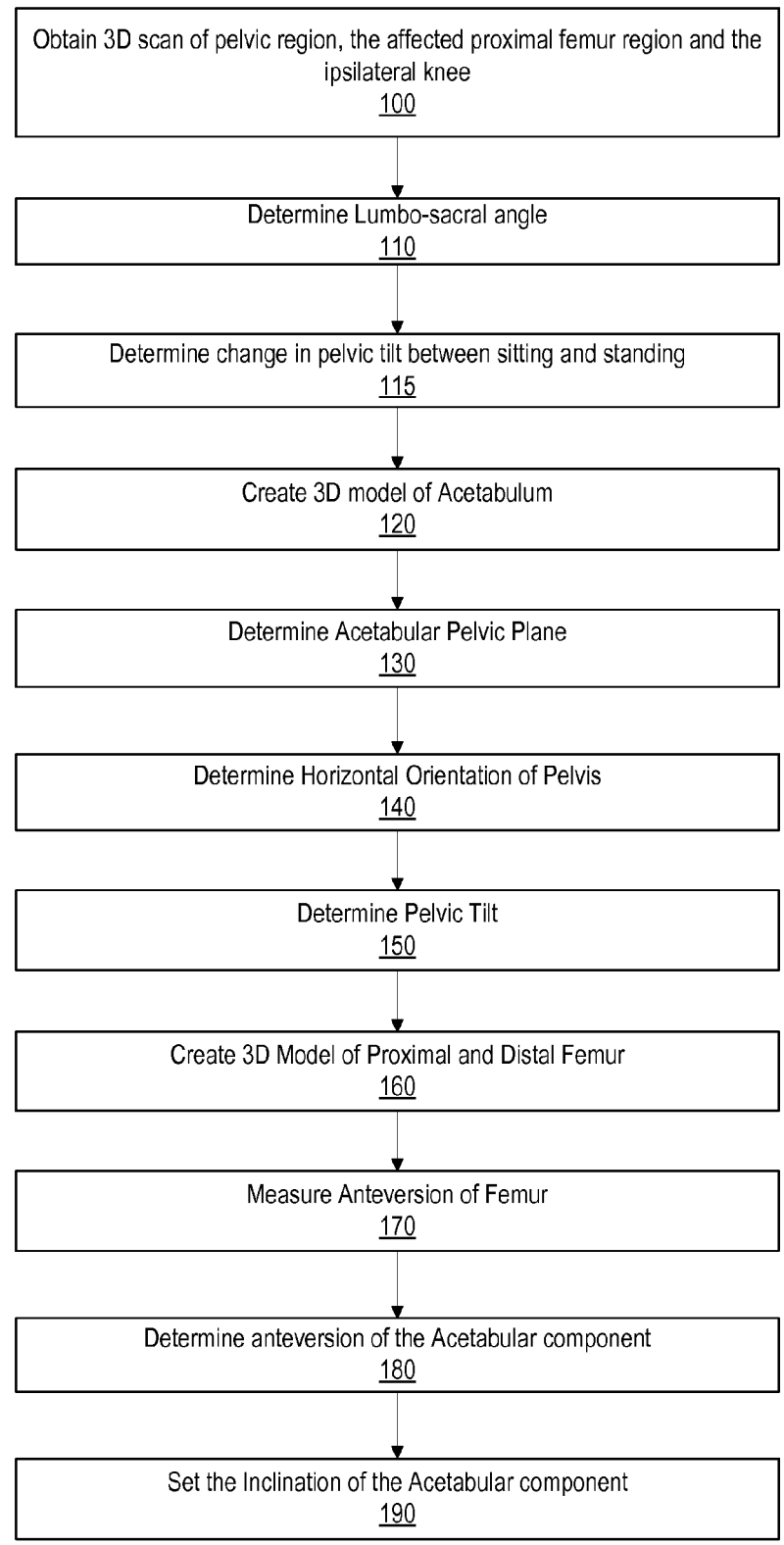
FIG. 3 is a flow diagram of a method in accordance with the present invention and relating to pre-operative imaging and reconstruction steps.

In accordance with the present invention, one exemplary imaging phase for determining proper orientation and implantation of an acetabular component (cup) involves the following pre-operative imaging steps as set forth in FIG. 3 and involves the use of the imaging system 100. According to a first step 100, a three dimensional (3D) scan of the patient's pelvis is obtained using conventional equipment such as a CT or MR device (the imaging system 100) to yield 3D imaging data that is subsequently used to construct a 3D model. In addition, the 3D scan of the patient's body can optionally include the affected proximal femur and the ipsilateral knee (the performance of this step depends on the technique to orient the acetabular component (cup)). The imaging system 100 forwards the 3D scan(s) to be stored as image data files in the memory (storage) 19 of the computer device 15.

At an optional second step 110, a sitting lateral radiograph is obtained to determine the lumbo-sacra angle which is the angle between the plane of the upper border of the sacrum and the horizontal or the angle from the anterior pelvic plane and the vertical. This step can be performed using conventional radiology equipment such as an x-ray device (imaging system 100). The result of the step 110 can also be stored in the memory 19 as image data (file). In other words, the imaging system 100 delivers the image data to the storage 19.

An additional optional step 115 involves determining the change in pelvic tilt between sitting and standing. This can be performed using conventional technology including obtaining a standing AP radiograph or standing lateral radiograph to determine the change in pelvic tilt (comparison between sitting and standing lateral radiographs). it will be appreciated and understood based on the present disclosure that steps 110, 115 are optional and depend upon which method (see below) is used to determine the proper orientation of the acetabular component.

3D Reconstruction Phase

In accordance with the present invention, the next phase is a 3D reconstruction phase in which one or more 3D models are generated using the data (images, etc.) collected in the above imaging phase. This phase is completed using suitable imaging and 3D software (applications 17, 21) as discussed herein which provides 3D modeling of collected data (images) and permits the 3D reconstructed image to be manipulated.

More specifically, as is known, 3D imaging software and other imaging software, as well, include a number of user tools that avow images to be easily manipulated. Some of the more popular tools are tools that: avow for rotation of the object in three dimensions, allow viewing of the object from any desired angle (even from the inside looking out), allow zooming in on a portion, allow cropping, allow parts to be made transparent or otherwise manipulated to show other components, etc. In addition, the software (application 21) can also produce 2D images using the inputted/captured information. In addition, distances and angles can be determined between points, planes, etc. defined by the user. For example, a pointer (tool) can be used to select a first point and then used to select a second point and a linear distance between the two points is calculated. Similarly, an angle can be determined between two defined planes.

More particularly, in step 120, a 3D model is created of the acetabulum, and optionally is created for the proximal femur and the distal femur (once again depending on the method selected for orienting the acetabular component). The 3D model can be generated using the modeling software as described above. As with the other models, this 3D model can be manipulated.

In step 130, an acetabular pelvic plane is created using both the anterior superior iliac spine (ASIS) and pubis. As is commonly understood, in total hip arthroplasty (THR), the orientation of the acetabular implant is expressed in terms of two angular measurements: the abduction and anteversion angles. Thus, in connection with hip arthroplasty, it is very desirable to accurately and quickly define the APP. The APP is suitably defined by 3 anatomical landmarks on the pelvis: the two anterior superior iliac spines (ASIS's) and the midpoint of the pubic tubercules. The anterior pelvic plane can thus be defined as the plane formed between a line joining both anterior superior iliac spines and the midpoint of the pubic tubercules. The horizontal X-axis is defined by the line connecting the teardrops or optionally, a line connecting the centers of the right and left hip joint, or optionally, a line connecting the bottom of the right and left inferior ramus of the ischium.

A coordinate system based on the APP is defined and can be used to determine the abduction and anteversion angles. The Y-axis is defined as a vertical line intersecting the midpoint of the pubic tubercules, and the cross-product of the X and Y axes defines the Z-axis. Abduction is defined as rotation about the Z-axis and anteversion is defined as rotation about the Y-axis. It will be readily appreciated that there are other definitions and expressions for the concepts of anteversion and abduction and the above definitions are merely exemplary.

In one embodiment, the step 130 can thus be carried out by manipulating the 3D model generated in step 120 and by the user (using a user interface tool such as a mouse) digitally marking the image with reference points corresponding to the left and right anterior superior iliac spines (left ASIS and right ASIS) and the midpoint of the pubic tubercules. After these points are marked, the system 10 of the present invention determines (using software) the plane containing these three reference points and stores in memory 12/storage 19, information representative of the plane for the image in relation to the reference image. Such plane constitutes the anterior plane of the acetabulum for the left and right hips.

Next in step 140, a horizontal orientation of the pelvis is determined using the acetabular teardrops. As is known, the acetabular teardrop is located inferomedially in the acetabulum, just superior to the obturator foramen. The lateral lip is the exterior, and the medial lip is the interior of the acetabular wall. The teardrop comprises a well-defined, constant portion of the medial acetabular wall. As with the other steps, this step is performed using imaging software that allows manipulation of 3D models, such as the 3D pelvis model (image). It will be appreciate that the above is merely one technique for determining the horizontal orientation of the pelvis and other techniques exist including fitting a sphere to the medial and lateral acetabulum and drawing a line between the centers.

At step 150, the pelvic tilt is determined and the degree (amount) of pelvic tilt is measured using the lateral radiographs that were obtained in step 110. As is understood in the art, pelvic tilt refers to the orientation of the pelvis in respect to the femurs it rests upon and in space. It can tilt in four basic directions, however, in the context of the present invention, only two of the directions are of interest, namely, 1) anterior pelvic tilt (pelvic flexion); and 2) posterior pelvic tilt (pelvic extension).

In accordance with the present invention and as discussed herein, the orientation of the acetabular component (cup) is referenced off of the pelvic position that is generated upon completion of the step 140.

At step 160, a 3D model is created of the proximal and distal femur. Once again, conventional 3D modeling software can be used to create this model.

Once the 3D model (3D reconstruction) of the femur is created in step 160, at step 170, the anteversion of the femur is measured from the 3D femur model. Femoral anteversion is measure of the "twist" of the femur. Femoral anteversion in accordance with the present method is determined by evaluating the degree of anteversion using the 3D model of the femur and other stored information. The degree of anteversion can be measured from this 3D model and can be stored in the memory 12/storage 19.

It will be appreciated and understood that the results of any of the preceding steps can be stored in the memory 12/storage 19 as images, as a collection of data (measurements), etc.

Acetabular Component (Cup) Orientation Phase

In accordance with the present invention, the next phase is one in which the orientation of the acetabular component (cup) is determined. In other words, the target orientation is selected. It is known that the acetabular cup orientation can be defined by two angles: abduction or inclination and anteversion. It is also known that there are a number of different techniques for determining the proper (desired) orientation of the acetabular component as discussed in more detail below. More specifically, several different techniques are described below for determining the proper (desired) orientation of the acetabular component; however, the practice of this phase of the present invention is not limited to the disclosed techniques since others can be used.

According to one orientation technique, in step 180, the anteversion of the acetabular component (cup) is determined by a set of prescribed equations. For example, for male patients, the anteversion can be determined by the following equation: 30°−femoral anteversion angle (result of step 180)=the cup anteversion. For example, for female patients, the anteversion can be determined by the following equation: 45°−femoral anteversion angle (result of step 180)=the cup anteversion. It will be understood that the proceeding equations are merely exemplary in nature and it is within the scope of the present invention that there can be some deviation therein. At step 190, the cup inclination is set at a prescribed value, such as 40°.

Figure 7A:
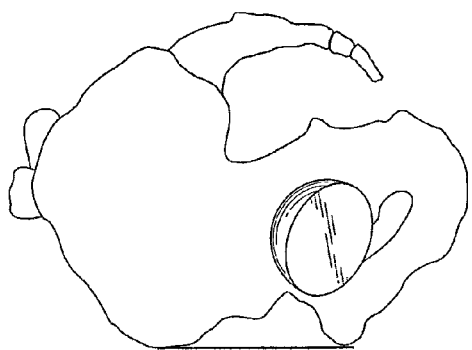
FIG. 7A-7C show an acetabular component oriented relative to the acetabulum according to a first method once the pelvis has been properly oriented.
Figure 7B:
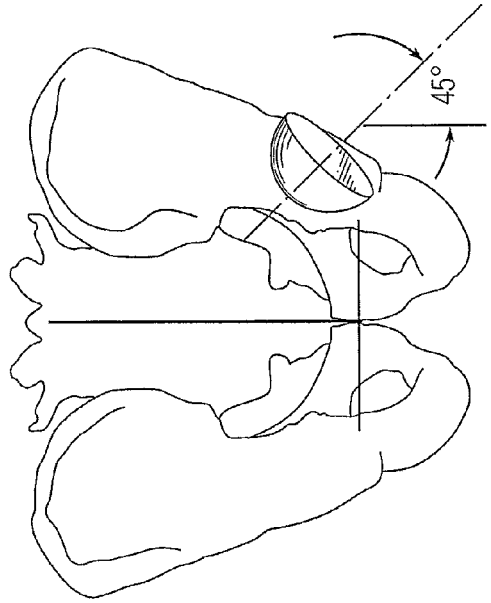
Figure 7C:
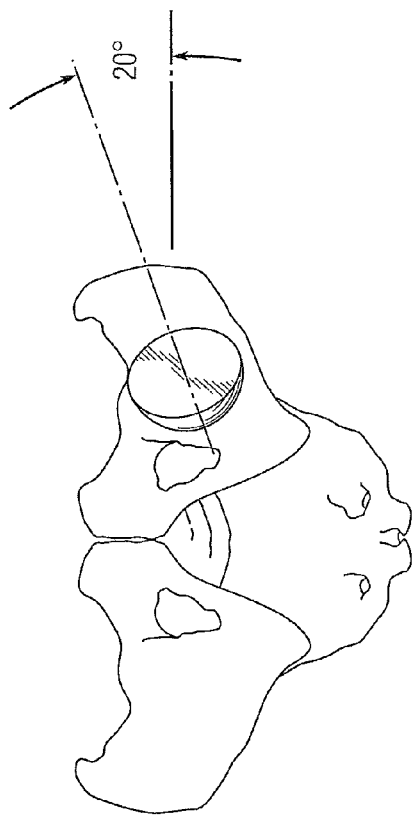
Figure 8A:
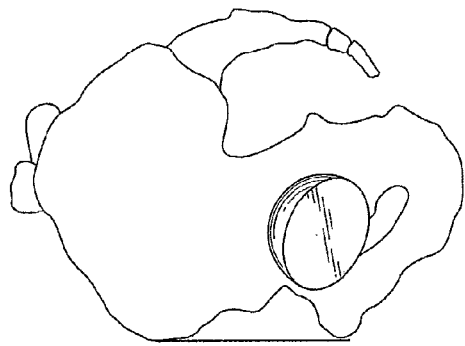
FIG. 8A-8D show an acetabular component oriented relative to the acetabulum according to a second method once the pelvis has been properly oriented.
Figure 8B:
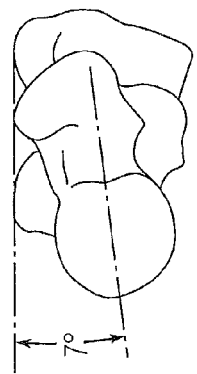
Figure 8C:
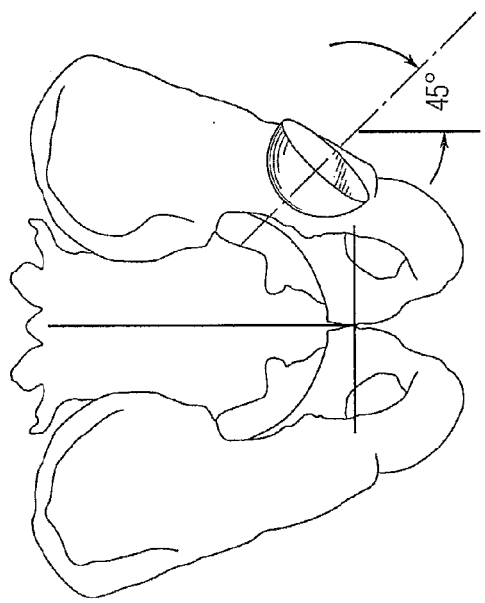
Figure 8D:
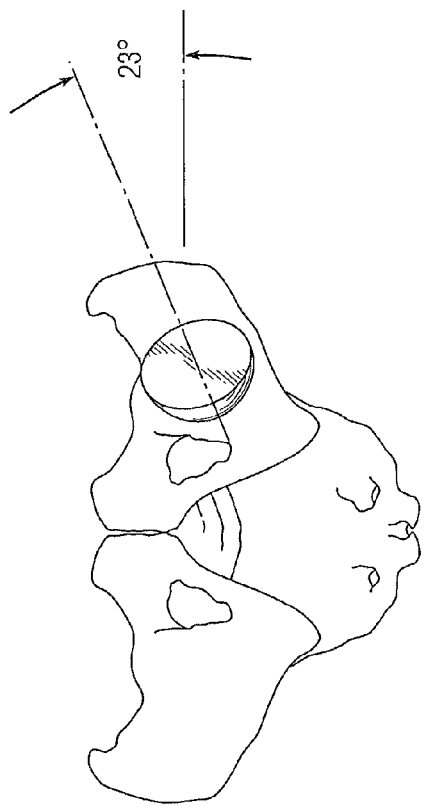

FIGS. 7A-C illustrate one technique for orienting the acetabular component and in particular, these figures show the acetabular component being oriented according to a prescribed anteversion angle (e.g., 20° as labeled or another prescribed angle) and a prescribed inclination angle (e.g., 45° as labeled or another prescribed angle). FIGS. 8A-8D illustrate another technique for orienting the acetabular component and in particular, these figures show a technique that incorporates steps 167-180 in that the acetabular component is oriented according to a calculated anteversion angle (see step 180) (e.g., 23° as labeled or another prescribed angle) and a prescribed inclination angle (e.g., 45° as labeled or another prescribed angle). FIG. 8D shows the calculation of the femoral anteversion angle (e.g., 7°) which according to the equation of step 190 results (for a male patient) in the anteversion being: 30°−7°=23° as shown.

The result of step 190 and this phase is that the orientation of the acetabular component (cup) is determined and this proper (target) orientation is used in subsequent steps as described below for forming the patient-specific guide.

Yet another method for determining the proper orientation of the acetabular component is based on the use of lateral radiographs and is shown in FIGS. 9A-9E. The amount of pelvic tilt can be calculated from sitting and standing lateral radiographs which are obtained using conventional imaging equipment. Patients that orient their pelvis in a more flexed position when sitting are at risk for anterior dislocation of their hip replacement as increasing the flexion of the pelvis effectively reduces the amount of anteversion of the acetabular component. In these patients, the anteversion of the acetabular component will be increased by 10 degrees (i.e., to approximately 30 degrees). This amount of increase is merely an example of how much the anteversion could increase. It could also be increased in proportion to the amount of increase in pelvic flexion.

In addition, the anteversion of the cup can be modified based on the orientation of the pelvis in the standing position (e.g., greater pelvic flexion, more anteversion of the acetabular component).

Design of Patient-Specific Instrument (Guide) and Surgical Procedure Phase

In accordance with the present invention, the next phase is one in which a patient-specific instrument (guide) is designed in view of the information captured in the proceeding phases and is constructed for simply, yet accurately, orient the acetabular component (cup) during TNR.

While patient-specific guides for acetabular cup positioning/orienting have been created in the past, the present invention provides a different approach in terms of the design of the patient-specific instrument that is used in the surgical procedure. More specifically and as will be appreciated below, previous instruments were developed by using the rim of the acetabulum to fit the patient-specific guide. The present invention teaches away from such approach due to the fact that at the time of surgery, the rim of the acetabulum is difficult to access as a result of it being covered in part by soft tissue (i.e., the labrum). As a result, a patient-specific guide that grasps the rim requires extensive soft-tissue resection. The present invention avoids this difficulty and provides an improved alternative approach.

First Embodiment—Predetermined Pin Method

Figures 5, 6:
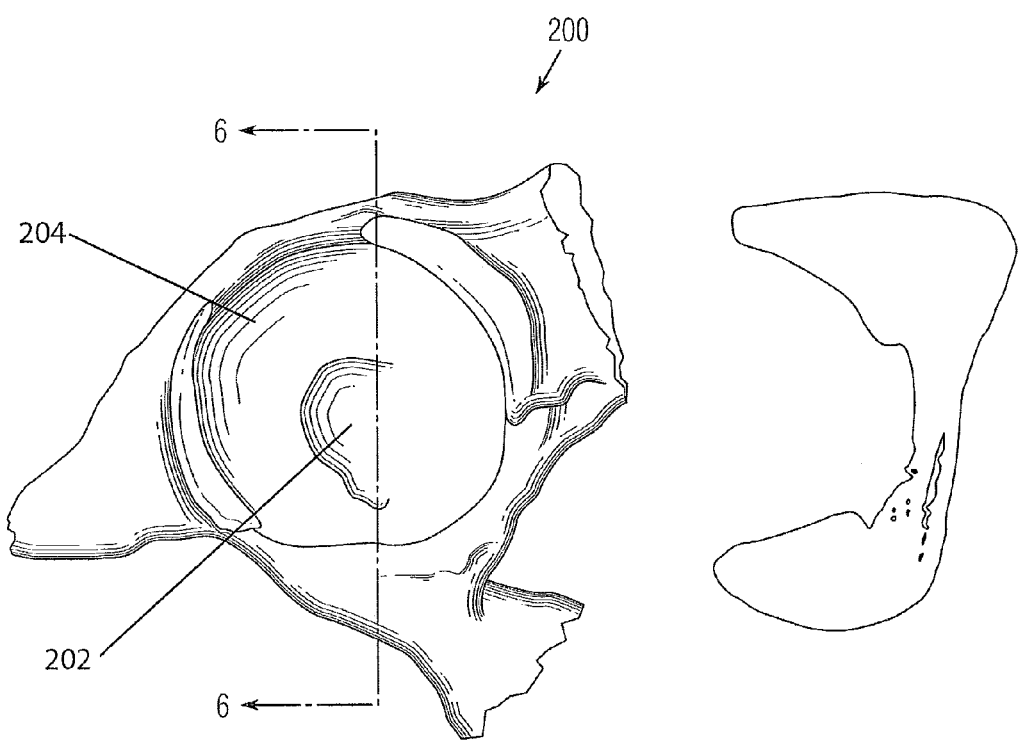
FIG. 5 is a top plan view of an acetabulum.
FIG. 6 is a cross-sectional view taken along the line 6-6 of FIG. 5.

FIG. 5 is a top plan view of a virtual representation of an acetabulum 200 that is produced using the proceeding imaging and modeling steps based on images obtained from the patient. As previously mentioned, the acetabulum 200 includes an acetabular notch 202 and a lunate surface 204. FIG. 6 is a cross-sectional view taken along the line 6-6 of FIG. 5 showing the acetabulum 200 and in particular, showing the acetabular notch 202 and the undercut nature thereof.

At step 300, a center of the virtual acetabulum is determined by fitting a sphere to the lunate surface 204 of the acetabulum (to be performed after step 120). Next at step 310, a virtual hemisphere 210 is placed at the center location and oriented according to one of the acetabular component orientation methods described herein. The result of step 310 is a centered and properly oriented virtual hemisphere that can then be modeled to form the patient-specific guide as discussed below.

The hemisphere 210 has a diameter that is larger, by a predetermined amount, than the sphere that was fit to the lunate surface 204. In one embodiment, the predetermined amount is approximately 5 mm; however, the diameter of the hemisphere 210 can be larger than 5 mm and similarly can be less than 5 mm. In other words, the 5 mm increase is exemplary and not limiting of the present invention.

Figure 11:
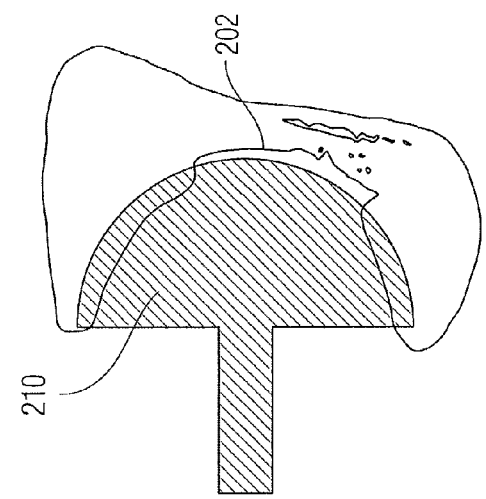
FIG. 11 is a cross-sectional view of FIG. 10.
Figure 10:
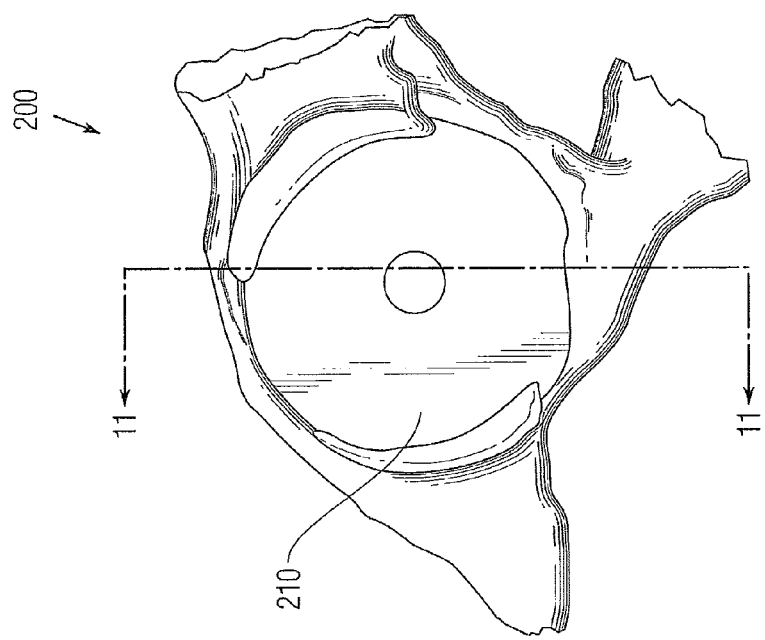
FIG. 10 is a top plan view of the acetabulum with a virtual representation of an acetabular guide having an initial hemispherical shape in accordance with one embodiment of the present invention inserted into the acetabulum.

As shown in the cross-sectional view of the FIG. 11, when the virtual hemisphere 210 is initially fit to the representation (3D model) of the acetabulum 200 and as shown, there are areas of interference between the virtual hemisphere 210 and the structure of the acetabulum representation 200. This is expected since as described above, the acetabulum does not have a perfect spherical shape and importantly, the floor of the acetabulum includes the notch 202 (the shape of which varies amongst patients). FIGS. 10 and 11 thus show one of the initial steps in the modeling (design) of the patient-specific acetabular guide. This step and others are performed by the software applications described herein which allows manipulation of the 3D model of the acetabulum including placement of another 3D representation (model), in this case the hemisphere 210, relative thereto.

Figure 3A:
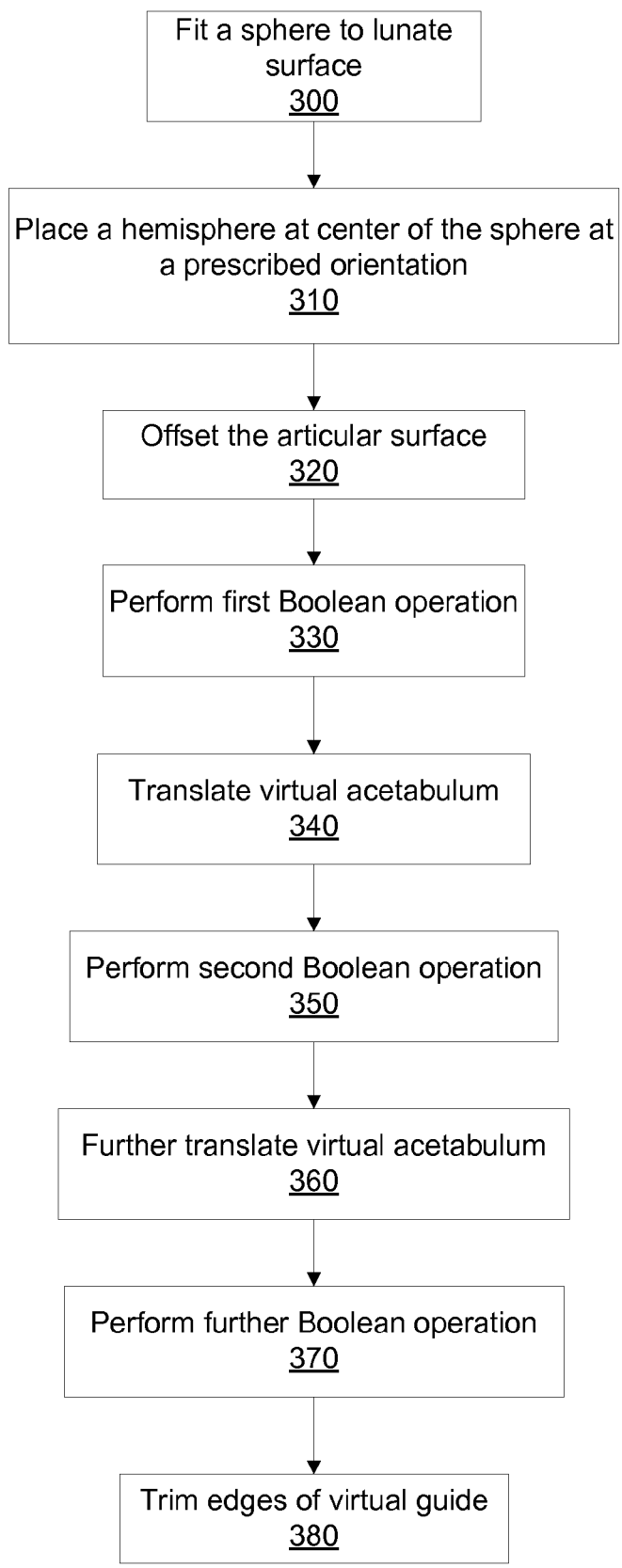
FIG. 3A is a flow diagram of a method in accordance with the present invention and relating to the design of the patient-specific acetabular guide.
Figure 12:
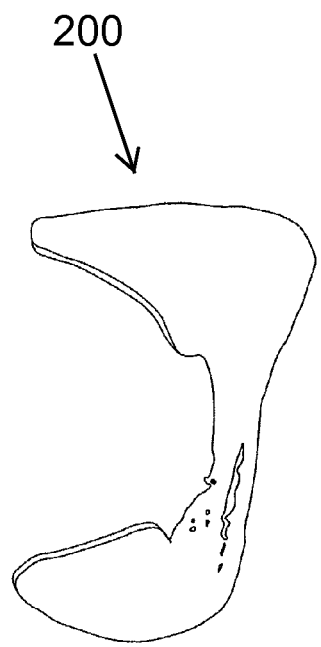
FIG. 12 is a cross-sectional view showing an articular surface of the acetabulum being virtually offset by a prescribed distance.

As shown in FIG. 12 and in accordance with step 320 (FIG. 3A), the articular surface of the virtual acetabulum 200 (i.e., the lunate surface 204) is offset a predetermined distance, such as, for example, about 1 mm. It will be appreciated that the predetermined offset distance can be entered by the user (designer) using the input device 110. The offset is thus relative to the virtual lunate surface of the acetabulum 3D model and is performed based on the inputted predetermined distance. The result (image) of this step and the other steps can be stored in memory 12/storage 19 and is displayed on display 120. The user can readily input different predetermined offset distances and the result is graphically shown on the display 120.

As described below, in accordance with the present invention, a series of Boolean operations are performed between the virtual hemispherical shaped guide (hemisphere 210) and the offset virtual acetabulum (3D model) to remove the part of the guide that interferes with bone and produce a model of a patient-specific acetabular guide which can then be manufactured.

As is known in the industry, Boolean operations can be used to create complex solid models out of primitives. In general, Boolean operations can include a number of different modeling operations including: 1) intersect: defines a new solid object based on the common volume between selected solids; 2) union: defines a new solid that consists of common and uncommon volume between selected solids; 3) subtract: select two set of solids. In addition, a single solid based on the removal of the second set from the first one will be created. All the above operations will eliminate the original solids.

In accordance with the present invention and as will be appreciated in view of the following disclosure, the present method includes performing at least one Boolean operation (and preferably a plurality of Boolean operations) to remove a portion of the virtual acetabular guide image (e.g., the hemispherical shaped guide) and then subsequently forming the actual patient-specific acetabular guide. As each Boolean operation is performed, one or more portions of the virtual acetabular guide image are removed and more specifically, virtual interferences between the acetabular guide image and the 3D acetabulum model (bone image) are at least partially removed from the material of the virtual guide.

In step 330, a first Boolean operation is performed between the virtual hemisphere 210 and the offset acetabulum (i.e., with the offset articular surface) to remove portions of the hemisphere 210 that interfere with bone (i.e., interfere with the acetabulum). The results of the first Boolean operation are the creation of virtual guide that has a contour that matches the articular notch 200 of the acetabulum representation (virtual image). FIGS. 13-15 show the results of the first Boolean operation and depict the modeled virtual guide 210 inserted into the virtual acetabulum and into contact with the offset articular surface.

Figure 16:
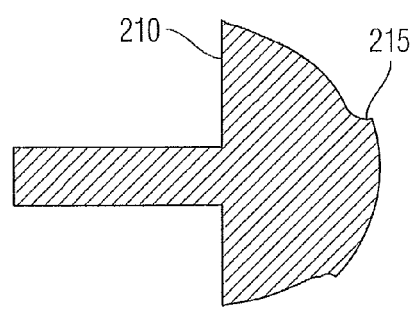
FIG. 16 is a cross-sectional view showing the acetabular guide of FIG. 13 removed from the offset acetabulum.

In FIG. 16, an undercut 215 is present along the bottom of the virtual hemispherical shaped guide 210 and this undercut 215 would prevent full insertion of the guide 210 into the acetabular notch.

The next steps and images reflect that in accordance with the present invention the Boolean operation is repeated n times in order to obtain a patient-matched guide 210 by continuously fine tuning the shape and contour of the guide 210 so that in accordance with the present invention and in direct contrast to prior art approaches, the virtual guide 210 (and subsequently, the physical guide itself) has a shape/contour that matches the acetabular notch.

In step 340, the virtual acetabulum (that is offset as a result of step 320) is translated a predetermined first distance along an center axis (i.e., an axis perpendicular to the face of the guide 210). In one exemplary embodiment, the predetermined first distance is 1 mm; however, it will be readily understood that the first distance be any number of other distances and the above value is not limiting of the present invention but is merely exemplary. It will further be understood that, as described herein, the predetermined first distance can be chosen in view of the value of n in that its value can be selected in view of the number of Boolean operations that will be performed during the guide modeling process. For example, and as discussed below, the predetermined first distance can be 1 mm in the event that there are four translation steps as part of the Boolean process discussed below. In other words, when there are four translation steps, the virtual offset acetabulum is translated in 1 mm increments four times.

Figure 17:
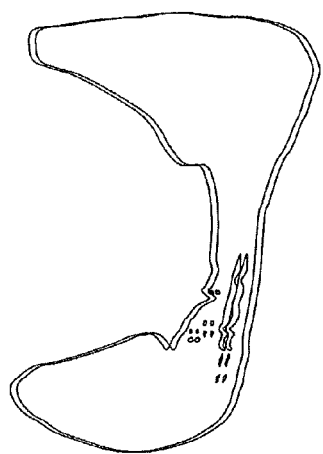
FIG. 17 is a cross-sectional view of the acetabulum translated a predetermined distance along an axis of the cup.

FIG. 17 shows the translation of the virtual offset acetabulum along the insertion (cup) axis.

Figure 18:
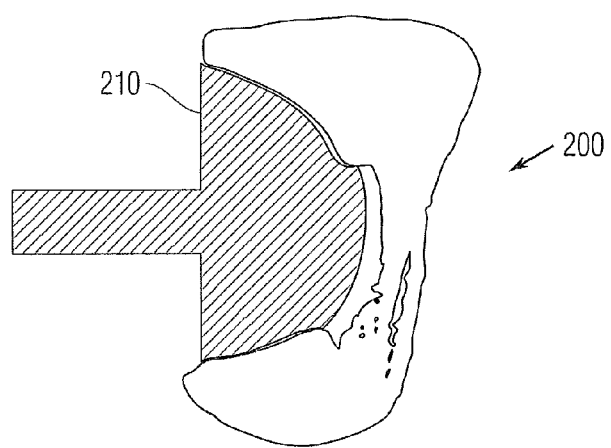
FIG. 18 is a cross-sectional view of the acetabulum showing the result of a second Boolean operation between the acetabular guide and the translated acetabulum of FIG. 17 showing modification to the guide to remove material interfering with bone.
Figure 19A:
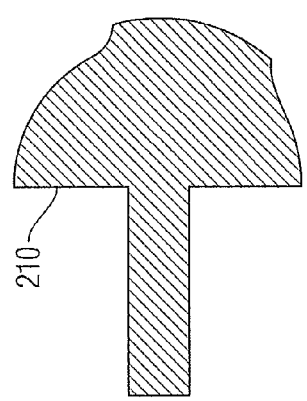
FIG. 19A is a cross-sectional view showing the acetabular guide of FIG. 18 removed from the translated acetabulum.
Figure 19B:
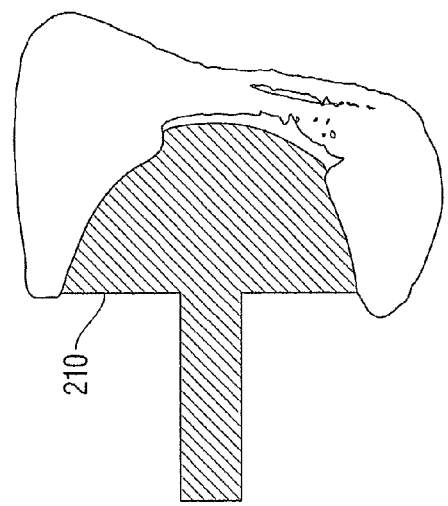
FIG. 19B is a cross-sectional view of the acetabular guide of FIG. 18 implanted into a virtual acetabulum showing a fit therebetween.
Figure 20:
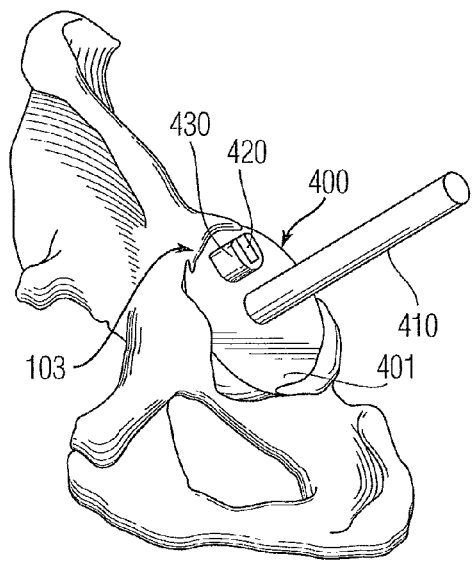
FIG. 20 is a perspective view of a first step of a surgical procedure, according to a first embodiment, in which the patient-specific guide in inserted into the acetabulum.

At step 350, a second Boolean operation is performed in the manner described above with respect to the step of performing the first Boolean operation. FIGS. 18 and 19A and 19B show the results of the second Boolean operation and depicts the matched guide 210 with the undercut nearly eliminated.

As best shown in FIG. 19A and 19B, the undercut 215 is nearly eliminated as a result of performing the second Boolean operation. FIG. 19B shows the matched guide 210 inserted into the virtual (patient-specific) acetabulum that is not translated according to step 340 to show the matched fit between the guide and the acetabulum.

As mentioned above, the present method includes additional steps 360 and 370 in which in step 360 the virtual acetabulum is further translated a predetermined second distance along the center axis. The first and second distances can be the same or can be different in one embodiment, When the distances are the same, the virtual acetabulum is thus translated in increments (that have the same distance) along the center axis. In step 370, an additional Boolean operation is performed on the result of step 360. The steps of 360 and 370 can then be repeated a number of additional times in order to subject the models to additional Boolean operations.

In one embodiment, five Boolean operations are performed in the design of the virtual acetabular guide 210. However, it will be appreciated that less than 5 Boolean operations can be performed or more than 5 Boolean operations can be performed to form a patient-specific (patient-matched) guide that matches the articular notch 202 but has removed a majority of the undercut, so that the guide can be implanted as discussed below. The entire undercut is not removed since it is desirable to have a slight undercut as this creates a locking effect between the guide and the acetabulum, thereby allowing the subsequently formed physical acetabular guide to snap into place within the acetabulum due to this locking effect with the articular notch. In other words, a sufficient amount of undercut is left to cause an interlocking between the guide and the acetabular notch.

At step 380, edges of the virtual acetabular guide 210 that extend onto the rim of the virtual acetabulum are trimmed and indicia (identification information) can be associated within the finished virtual guide (or alternatively, the identification information can be initially stored in memory and then later placed on the actual physical guide when it is formed). This step 380 is important since the patient-specific guide that is made in accordance with the present invention does not rest on or utilize the rim of the acetabulum as a support surface but instead is matched to the acetabular notch as a means for attaching the guide to the acetabulum. In other words, the present guide is not modeled and manufactured (matched) based on the characteristics of the patient's acetabulum rim.

The results of steps 300-380 (the Boolean operations) can be saved in memory 12/storage 19.

Final Design—First Embodiment

Now referring to FIGS. 20-23, once the Boolean operations are completed, a final virtual acetabular guide is created and is stored in the memory 12/storage 19. This final virtual acetabular guide is patient-specific and serves as the basis for creating a physical patient-specific acetabular guide 400 that has the characteristics of the virtual acetabular guide and is used during the THR surgical procedure to more precisely locate and orientate the acetabular implant (cup) in the prepared acetabulum of the patient. Any number of different conventional techniques can be used to form the physical patient-specific guide 400, including but not limited to conventional molding techniques, additive manufacturing, or other forming techniques (to form guide that can be sterilized, preferably via an autoclave).

It will be appreciated that the patient-specific guide is thus modeled in view of the selected (optimal) orientation of the acetabular component and thus, said orientation is incorporated into the design of the guide.

A handle 410 is fixedly attached to guide 400 perpendicular to a face 401 thereof (i.e., perpendicular to the guide body). The handle 410 can then be used as a reference for the correct orientation of the acetabular component (i.e., implant 500 of FIG. 28). A slot 420 is formed in the patient-specific guide 400 using conventional processing techniques including conventional cutting (machining) techniques. The slot 420 is radially offset from the handle 410 and is located between the handle 410 and a peripheral edge of the guide 400. As shown, the slot 420 can be formed in a raised portion 430 that extends outwardly from the face 401 of the guide 400. The raised portion 430 can be formed during the process of forming the guide 400 itself (e.g., formed in a common mold) and slot 420 can be formed at that time or subsequently formed.

Figure 21:
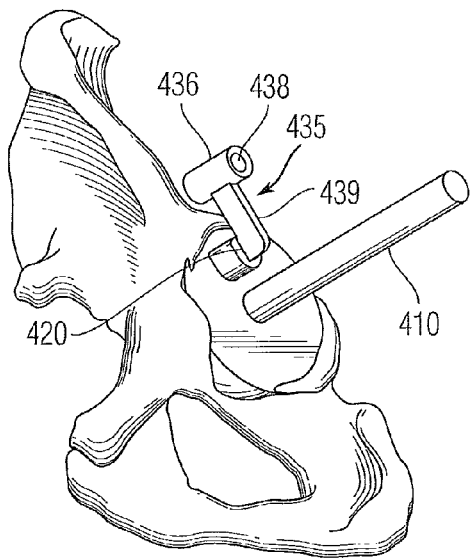
FIG. 21 is a perspective view of a second step of the surgical procedure in which a pin guide is coupled to the patient-specific guide.

As shown in FIG. 21, the slot 420 is configured for receiving a tool 435 that receives an axis pin 440 (FIG. 22) and more specifically, the tool 435 can be in the form of an axis pin guide that includes a base portion 436 that has a central bore 438 formed therethrough and open at both of its ends. The base portion 436 is thus a generally tubular structure. The central bore 438 slidingly receives the pin 440. The pin guide 435 also includes an extension (arm) 439 that extends radially outward from the base 436 and is orientated perpendicular to the base 436. At a free distal end of the extension 439, a coupling member (not shown) is formed and is configured to be received within the slot 420 so as to couple the pin guide 435 to the guide 400.

Figure 22:
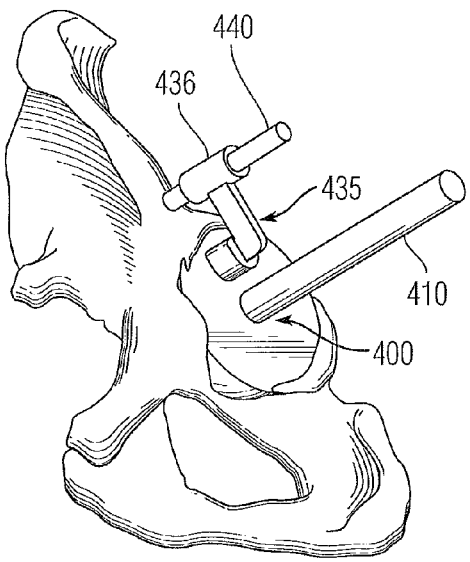
FIG. 22 is a perspective view of a third step of the surgical procedure in which an axis pin is inserted into the pin guide and is attached to the superior region of the acetabulum.
Figure 23:
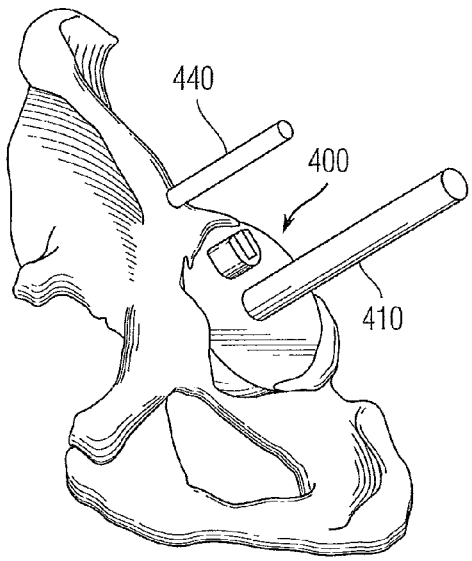
FIG. 23 is a perspective view of a fourth step of a surgical procedure in which the pin guide is removed and the patient-specific guide is ready for removal as well.
Figure 24:
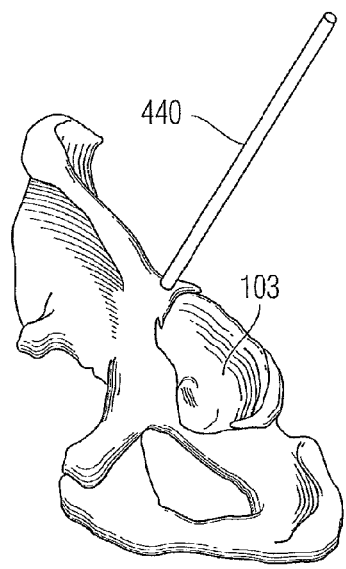
FIG. 24 is a perspective view of a first step of a surgical procedure, according to a second embodiment, in which a pin is placed arbitrarily within the superior region of the acetabulum.
Figure 25:
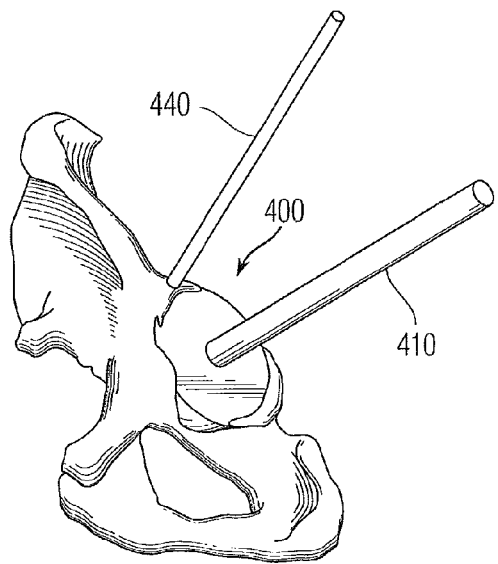
FIG. 25 is a perspective view of a second step of the surgical procedure in which the patient-specific guide in inserted into the acetabulum.

The pin guide 435 thus orients the axis pin 440 and allows the pin 440 to be fixedly attached to the superior acetabulum as shown in FIG. 22. It will be understood that the construction of the pin guide 435 and the manner of attachment of the pin guide 435 to the acetabular guide 400 constrains and causes the pin 440 to be oriented in a parallel axis relative to the axis of the 410 handle of the guide 400.

For the operative procedure itself, tissue in the acetabular notch 202 is debrided. The patient-specific (patient-matched) guide 400 is pressed into the acetabulum. The guide 400 should snugly fit within the acetabulum due to the locking between the guide 400 and the acetabular notch 202 in accordance with the teachings of the present invention. The pin guide 435 is mated to the guide 400 by inserting the coupling member of the extension 439 into the slot 420 and then the pin 440 is inserted into the bore 438 and using conventional techniques, the pin 440 is fixed to the superior acetabulum. Once the pin 440 is fixed to the superior acetabulum, the pin guide 435 is removed (FIG. 23) and then the guide 400 is removed. The result is that axis pin 440 is placed and is parallel to the cup impactor axis (i.e., the axis of the handle 410).

Figure 28:
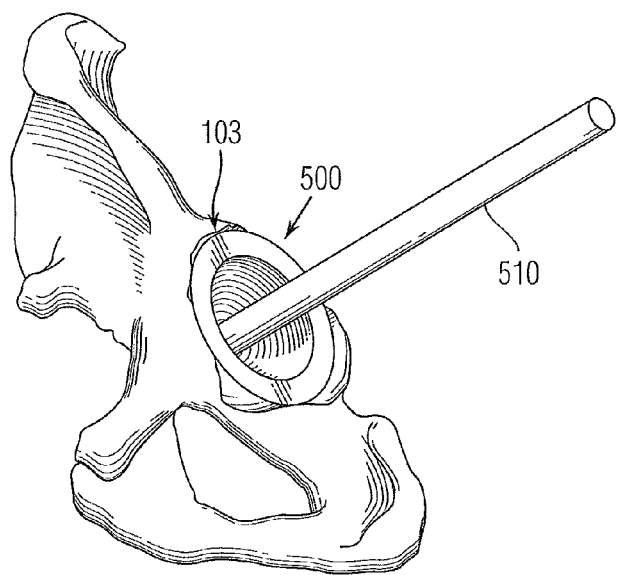
FIG. 28 is a perspective view of an acetabular component (implant) implanted within the acetabulum.

Next and as shown in FIG. 28, the acetabulum is prepared for receiving the acetabular component 500 (impactor/implant) using conventional surgical processing techniques. For example, a sufficient amount of the bone of the acetabulum is removed in order to prepare a contact surface for the acetabular component 500 that will be engaged thereto. The step can involve using bone reaming techniques, etc. After the acetabulum is reamed, the acetabular component 500 is accurately implanted in the acetabulum by visually confirming that the axis (e.g., defined by handle, 510) of the acetabular component 500 is parallel to the axis of the pin 440. The acetabular component 500 is then affixed to the acetabulum with a fastening means by press-fitting the acetabular component 500 to the bone or using a screw, for example. The screw is positioned through a hole in the acetabular component 500 as is known. The pin 440 is then removed.

Second Embodiment—Arbitrary Pin Method

The physical patient-specific guide 400 that is produced in accordance with the preceding teachings is also used in the arbitrary pin method. The pre-determined pin method according to the first embodiment can at times be difficult to implement in actual practice for the following reasons. It can be difficult to place the axis pin (pin 440) in the superior region of the acetabulum such that it is parallel to the center axis. Also, steps that are followed in an exemplary THR surgical procedure already include placing a superior pin for soft tissue retraction and the placement of a second pin, namely, the axis pin 340 can be difficult due to spacing and overcrowding.

FIGS. 24-27 show the steps associated with this second embodiment. In addition to the axis pin 440 and the patient-specific guide 400, a second instrument (pin reference device) 600 is used. The second instrument 600 is in the form of a rod aligner instrument and is defined by a rod positioner portion 610 and an adjustable rod 700 that is movably coupled thereto and has a number of different degrees of motion to allow adjustment and orienting of the rod 700 relative to the rod positioner portion 610. The rod positioner portion 610 includes a body having a bore 612 formed therein for receiving the axis pin 440. The rod positioner portion 610 can slidingly travel along the axis pin 440 which is indicated by arrow A showing movement in a linear direction. The rod positioner portion 610 can also rotate about the fixed axis pin 440 as indicated by arrow B. It will be appreciated and understood based on the following discussion that the second instrument 600 can be coupled (attached) to the axis pin 440 after the pin 440 is fixedly attached to the bone.

One end of the rod 700 is pivotally attached to the rod positioner portion 610 at a pivot 620. The rod 700 pivots about this pivot 620 as indicated by the arrow E and thus, the orientation of the rod 700 relative to the rod positioner portion 610 can be changed by such pivoting. As shown, the rod 700 can have two distinct sections of different shape, namely, a first section that mates directly with the rod positioner portion 610 and a second section that extends outwardly therefrom and serves as a reference axis as discussed below.

In one embodiment, the rod 700 is manipulated so as to orient the rod 700 in an orientation in which it is parallel to the axis of the guide 400 and more specifically, is parallel to the axis of the handle 410. This alignment can be done by the eye and it will be appreciated that the oriented rod 700 (parallel to handle axis) serves as a reference axis for placement of the implant 500 in the same manner described above. After orienting the rod 700, the instrument 600 is removed.

While not shown, it will be understood that the various parts of the second instrument 600 can be locked in their preferred orientations using conventional locking means, such as a locking screw or other mechanical locking mechanism. More specifically, once the proper orientation of the rod 700 is determined, the three degrees of freedom (represented by arrows A, B, and E) are locked so as to fix the orientation of the second instrument 600.

Figure 26:
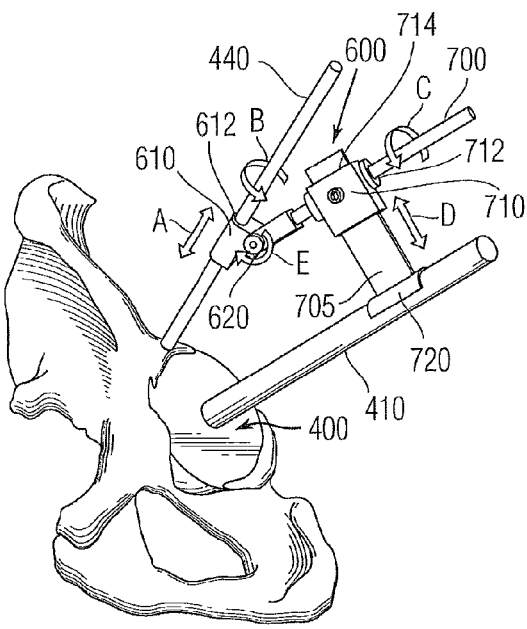
FIG. 26 is a perspective view of a third step of the surgical procedure in which an in which a rod aligner mechanism is connected to the pin and mated with the patient-specific guide and a reference rod is inserted into the rod aligner.
Figure 27:
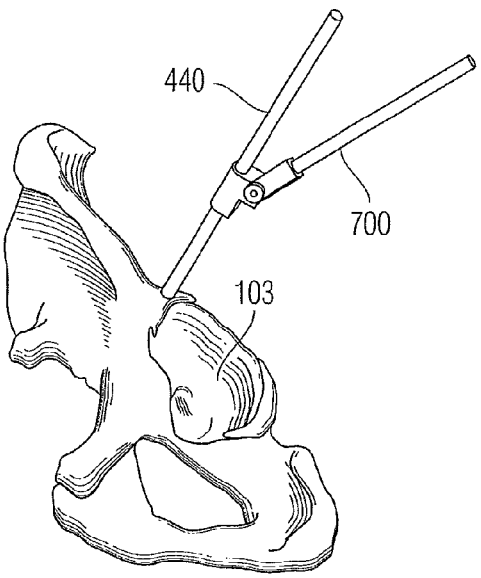
FIG. 27 is a perspective view of a fourth step of a surgical procedure in which the rod aligned mechanism and the patient-specific guide are removed.

The orienting of the rod 700 can also be assisted by the use of an additional component and more specifically, as shown in FIG. 26, the second instrument 600 can also include a rod aligner 705 that serves to couple and orient the rod 700 relative to the axis of the handle 410. The rod aligner 705 includes a body having a first section 710 at a first end that is configured as a rod receiving section and is defined by a body having a bore 712 formed therein and a slot 714 for receiving the end of the body of the aligner 705. The bore 712 is formed in the first section 710 and is configured to receive the rod 700 in a sliding manner through the slot 714. In other words, the rod aligner 705 can be mated with the rod 700 by sliding the first section 710 over the rod 700. The rod aligner 705 includes a second section in the form of a clamp-like structure 720 that has a concave surface that matches the cylindrical diameter of the handle 410. The structure 720 is thus mated to the handle 410 by pressing the clamp 720 into contact with the handle 410. The clamp 720 can thus assemble to the handle 410. The axis of the bore formed in the first section 710 and the axis of the handle (which can also be defined by a central axis of the clamp 720) are constrained to being parallel to one another and thereby, the rod 700 that passes through the bore in the first section 710 is caused to be parallel to the axis of the handle 410.

The rod aligner 705 can rotate relative to the rod 700 as represented by arrow C. Arrow D shows movement of the rod aligner 705 in a linear direction away/toward the handle 410.

As discussed above, all of the degrees of freedom of the second instrument 600 can be locked in the desired orientation using the locking means (e.g., screws). Thus, degrees of freedom (arrows A-E) are locked in place.

Once properly positioned, the rod aligner 705 is removed from the rod 700 and thus also disengages the handle 410 and the guide 400 is removed, thereby leaving the rod 700 as the reference axis for placement of the implant 500 in the same manner described above. Since all of the degrees of freedom of the second instrument 600 can be locked in place including the locking of the section 710, the removed rod aligner 705 can then be later installed back on the rod 700 and when properly oriented, contacts the impactor handle 510 (FIG. 28).

Thus, the rod aligner device 700 allows for a final verification step in which once the implant 500 is placed, the surgeon can check the orientation of the implant 500 using the rod aligner device 700. The clamp 720 can be attached to the cup impactor to assure that the cup impactor has oriented the cup according to the preoperative plan.

As discussed herein, the term "interlockingly mates" generally means to lock or join to one another and as described herein, because the entire undercut of the patient-specific guide is not removed, a locking or joining effect between the guide and the acetabulum is created, thereby allowing the physical patient-specific acetabular guide to snap into place within the acetabulum due to this locking effect with the articular notch. Interlockingly mates is not limited to an irreversible interlock but instead can apply to situations, as in the present invention, in which the patient-specific acetabular guide can be disengaged from the acetabulum and in particular from the acetabular notch structure.

Figure 30:
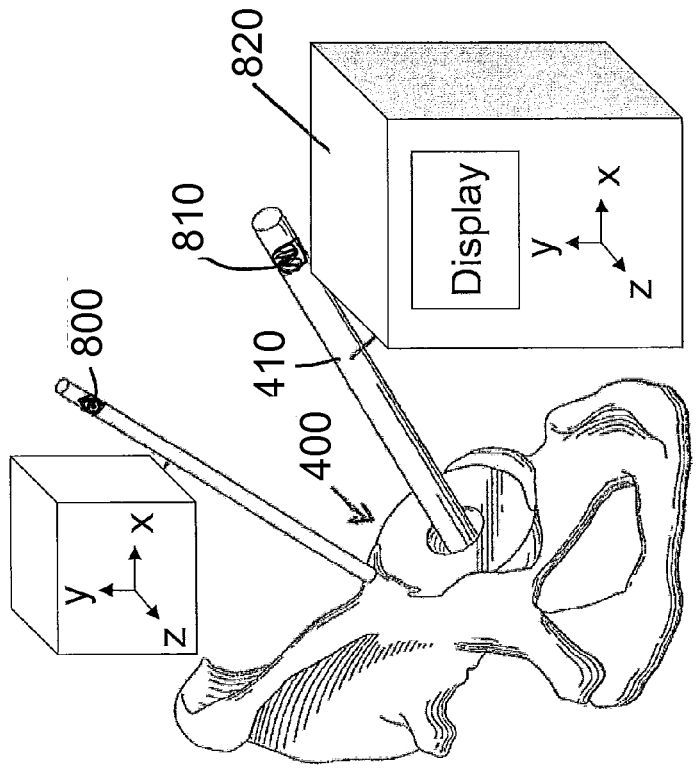
FIG. 30 is a perspective view of a second step of a surgical procedure, according to a third embodiment, in which the patient-specific guide in inserted into the acetabulum.
Figure 29:
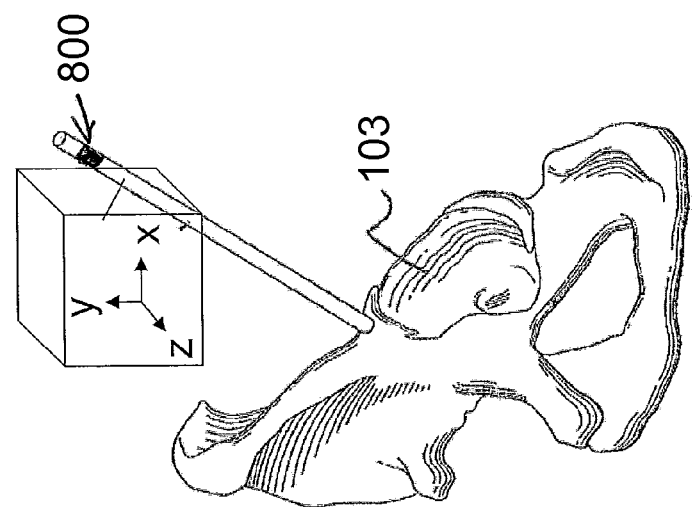
FIG. 29 is a perspective view of a first step of a surgical procedure, according to a third embodiment, in which a fiducial (instrument), with a known coordinate system, is placed within the superior region of the acetabulum.
Figure 31:
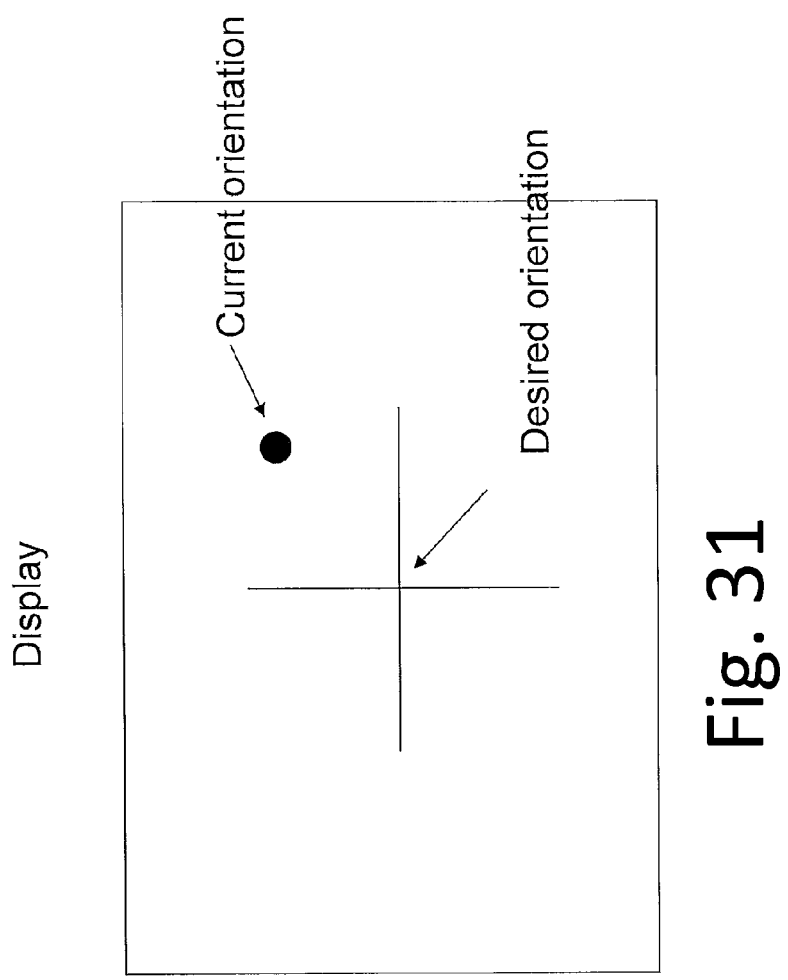
FIG. 31 is a schematic of a display showing a current location of the fiducial and the target (intended) location of the fiducial.

FIGS. 29-31 illustrate, another embodiment for orienting the acetabular component 500. In this embodiment, an orientation sensor 800 is rigidly fixed to the acetabulum 103. This sensor 800 can be attached via a pin (as shown), or directly to the bone with screws. It must be rigidly attached to the acetabulum 103 and be able to be removed. The orientation sensor 800 is defined by a first known coordinate system (including the orientation thereof in 3D space). The orientation sensor 800 communicates with a second sensor 810 that is connected to the handle 410 of the patient specific guide 400. This second sensor 810 receives an orientation signal from the orientation sensor 800 fixed to the acetabulum 103. The second sensor 810 can thus be defined by a second known coordinate system (including the orientation thereof in 3D space) relative to the first known coordinate system of the first sensor and therefore, the orientation can be tracked.

It can be either a wireless connection or a direct cable connection between the sensors. The patient specific guide 400 is inserted into and oriented within the acetabulum 103 and the second sensor 810 is rigidly fixed to the guide 400. However, it will be appreciated that the order of operations could go either way, the second sensor 810 can be rigidly fixed to the guide 400 then positioned into the acetabulum 103, or the guide 400 can be positioned into the acetabulum 103 and then the second sensor 810 rigidly fixed to the guide 400.

This system is thus part of a computer system and includes a display 820.

At this time, when the guide 400 is in the prescribed orientation in the acetabulum, the display on the sensor is 'zeroed' out, indicating the target orientation of the acetabular component 103 which is to be subsequently implanted. The coordinate system associated with the target orientation is thus saved in memory either as part of a computer system or memory of the second electronic device. The guide 400 is removed, and the acetabulum 103 is prepared. Now the second sensor 810 is rigidly attached to the impaction instrument 500 (FIG. 28). The orientation of the instrument (implant) 500 is adjusted until the saved target orientation is reached (i.e., when the stored known coordinate system are achieved). A display on the instrument (second sensor 810) can be used to help with the orientation procedure as shown in FIG. 31 (real time tracking and display of the orientation of the object to which the second sensor is attached). Alternatively, a series of numerical values could be on the display 820 to indicate when the target orientation has been reached. Once the cup has been impacted and its orientation verified, the first sensor 800 can be removed from the acetabulum 103.

In one embodiment, the sensors 800, 810 can thus communicate with a computer (machine) that executes software such as 3D positioning (coordinate) software and the 3D coordinates of the sensors 800, 810 are tracked and displayed on display 820. In this configuration, the sensors 800, 810 communicate with the computer system.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A method for forming a patient-specific acetabular guide for use in orienting an acetabular component with respect to an acetabulum of a patient as part of a surgical procedure, the method comprising the steps of:
    obtaining at least one image of the patient including at least 3D image data of a pelvic region of the patient;
    constructing a three-dimensional (3D) virtual model of an acetabulum of the patient based on the 3D image data of the pelvic region and based on a prescribed orientation of the acetabular component;
    constructing an initial patient-specific virtual acetabular guide;
    performing one or more modeling operations on the initial patient-specific virtual guide in view of the 3D virtual model of the acetabulum so as to form a final patient-specific virtual guide which has a bottom surface which has a portion that is shaped and configured based on the 3D virtual model of the acetabulum to initimately receive and interlockingly mate with an acetabular notch of the patient's acetabulum for attaching the patient-specific guide to the acetabulum according to the prescribed orientation; and
    forming the patient-specific acetabular guide based on the final patient-specific virtual guide.

2. The method of claim 1, wherein the step of constructing the initial patient-specific virtual acetabular guide comprises the step of first fitting a sphere to a lunate surface of the three-dimensional model of the acetabulum and then subsequently inserting a hemisphere into the three-dimensional model of the acetabulum at a center of the sphere and at the prescribed orientation, the hemisphere having a diameter greater than a diameter of the sphere.

3. The method of claim 1, wherein the step of performing one or more modeling operations on the initial patient-specific virtual guide includes the steps of:
    offsetting the lunate surface of the three-dimensional model of the acetabulum by a first predetermined distance; and
        performing at least one Boolean operation between the hemisphere and the offset three-dimensional model of the acetabulum to remove portions of the hemisphere that are in interference with a bony surface of the 3D virtual model of the acetabulum.

4. The method of claim 1, wherein the step of performing one or more modeling operations on the initial patient-specific virtual guide comprises the step of removing portions of the initial patient-specific virtual guide that are in interference with bony surface of the 3D virtual model of the acetabulum.

5. The method of claim 4, wherein the one or more modeling operations comprises a plurality of Boolean operations that are performed sequentially on the three-dimensional model of the acetabulum, wherein a second Boolean operation and any Boolean operations performed subsequent thereto are performed subsequent to the three-dimensional model of the acetabulum being incrementally translated along an center axis.

6. The method of claim 5, wherein the three-dimensional model of the acetabulum is translated along the center axis in a plurality of increments, each increment being about 1 mm.

7. The method of claim 5, wherein at least three Boolean operations are performed and incremental translation of the three-dimensional model of the acetabulum results in the bottom contact surface matching the acetabular notch of the patient's acetabulum but including a sufficient undercut to provide a locking effect between the bottom contact surface and the acetabular notch of the patient's acetabulum.

8. The method of claim 1, further including the step of trimming edges of the patient-specific acetabular guide that extend onto a rim of the patient's acetabulum.

9. A method of pre-operatively planning the implantation of a patient-specific acetabular component comprising the steps of:
    obtaining three-dimensional image data of a pelvic region of the patient;
    using the obtained image data to determine a prescribed orientation of the acetabular component with respect to an acetabulum of the patient, the prescribed orientation being defined by a center longitudinal axis; and
    constructing a three-dimensional model of an acetabular guide from the obtained image data, wherein the three-dimensional model of the acetabular guide includes a contact surface that includes a first portion that is shaped to substantially match an acetabular notch of the patient's acetabulum, wherein a center longitudinal axis of the acetabular guide is co-linear or parallel to the center longitudinal axis of the acetabular component, wherein the acetabular guide is configured such that when the acetabular component obtained from the three-dimensional model is inserted into the acetabulum, the first portion is directly engaged to the acetabular notch and includes a sufficient undercut to provide a locking effect between the first portion and the acetabular notch.

10. A method for implanting an acetabular component in an acetabulum of a patient comprising the steps of:
    inspecting a pre-operative plan including a three-dimensional image of the specific patient;
    selecting a prescribed orientation of the acetabular component;
    constructing a patient-specific acetabular guide having a contact surface that is made to conform to an acetabular notch of the acetabular of the patient in accordance with the three-dimensional image of the specific patient and the prescribed orientation;
    orienting the patient-specific acetabular guide in the acetabulum of the specific patient such that the contact surface interlocks with the acetabular notch of the patient's acetabulum;
    using the patient-specific guide to orientate a first reference member that defines a reference axis that is parallel to a center axis of the acetabular component; and
    implanting the acetabular component using the first reference member as a reference;

attaching a pin to a superior portion of the acetabulum; and coupling a pin reference device to the pin by passing the pin through a bore formed in a first section of the pin reference device, the first section of the pin reference device having two degrees of freedom relative to the pin and the pin reference device further including a rod that is pivotally attached to the first section, wherein the rod comprises the first reference member and defines the reference axis for orienting the acetabulum component within the acetabulum.

11. The method of claim 10, wherein the prescribed orientation is based on a patient-specific anterversion angle and an inclination angle.

12. The method of claim 11, wherein the patient-specific anteversion angle is increased by a predetermined amount of degrees a pelvis of the patient flexes during sitting as determined by an image of the patient.

13. The method of claim 10, wherein the step of selecting a prescribed orientation of the acetabular component comprises the steps of:

obtaining a sitting lateral radiograph;

obtaining a standing lateral radiograph; and determining a change in pelvic tilt based on the sitting and standing radiographs, the prescribed orientation being selected based on the change in pelvic tilt.

14. The method of claim 10, further comprising the steps of:

inserting a pin guide into an opening formed in a surface of the patient-specific acetabular guide that is opposite the contact surface, the pin guide having a pin receiving section that has a bore defined by a first axis that is parallel to an axis of the handle of the patient-specific acetabular guide;

inserting an axis pin through the bore, the axis pin comprising the first reference member;

fixedly attaching the axis pin to a superior portion of the acetabulum; and removing the pin guide from the patient-specific acetabular guide and removing the patient-specific acetabular guide from the acetabulum, whereby the axis pin defines the reference axis for orienting the acetabulum component within the acetabulum.

15. A method for implanting an acetabular component in an acetabulum of a patient comprising the steps of:

inspecting a pre-operative plan including a three-dimensional image of the specific patient;

selecting a prescribed target orientation of the acetabular component;

constructing a patient-specific acetabular guide having a contact surface that is made to conform to an acetabular notch of the acetabular of the patient in accordance with the three-dimensional image of the specific patient and the prescribed target orientation;

orienting the patient-specific acetabular guide in the acetabulum of the specific patient by attaching a first electronic device to the superior acetabulum, the first electronic device being defined by a first known coordinate system, wherein the patient-specific guide includes a second electronic device removably attached thereto, wherein when the acetabular guide is inserted into the acetabulum at the prescribed target orientation in which the contact surface interlocks with the acetabular notch of the patient's acetabulum, the second electronic device is defined by a second known coordinate system which is defined relative to the first electronic device and which is saved in memory;

removing the patient-specific guide from the acetabulum and removing the second electronic device from the patient-specific guide;

attaching the second electronic device to the acetabular component;

preparing the acetabulum for receiving the acetabular component; and moving the acetabular component in the prepared acetabulum until the second electronic device is defined by the saved second known coordinate system, thereby representing that the acetabular component is at the prescribed target orientation.

16. The method of claim 15, wherein the first and second electronic devices comprise first and second orientation sensors, respectively, that communicate with one another.

17. The method of claim 16, wherein second orientation sensor includes a display that shows in real time a current orientation of the second orientation sensor relative to the prescribed target orientation and guides a user to the prescribed target location at which indicia for the current orientation is superimposed on indicia for the prescribed target orientation.

* * * * *